US011414531B2

(12) United States Patent
Jayaratne et al.

(10) Patent No.: US 11,414,531 B2
(45) Date of Patent: Aug. 16, 2022

(54) NUCLEATING AGENTS, METHODS FOR THEIR PRODUCTION, AND ASSOCIATED POLYMER COMPOSITIONS

(71) Applicants: BASF SE, Ludwigshafen am Rhein (DE); Micronisers Pty Ltd, Dandenong (AU)

(72) Inventors: Vidura Nalin Jayaratne, Dandenong (AU); Terence William Turney, Dandenong (AU); Murray Horton, Nantwich (GB); Raphael Dabbous, Kaisten (CH)

(73) Assignees: BASF SE, Ludwigshafen am Rhein (DE); Micronisers Pty Ltd, Dandenong (AU)

( * ) Notice: Subject to any disclaimer, the term of this patent is extended or adjusted under 35 U.S.C. 154(b) by 269 days.

(21) Appl. No.: 16/609,962

(22) PCT Filed: May 2, 2018

(86) PCT No.: PCT/EP2018/061201
§ 371 (c)(1),
(2) Date: Oct. 31, 2019

(87) PCT Pub. No.: WO2018/202707
PCT Pub. Date: Nov. 8, 2018

(65) Prior Publication Data
US 2020/0079929 A1 Mar. 12, 2020

(30) Foreign Application Priority Data
May 3, 2017 (AU) ................ 2017901604

(51) Int. Cl.
C08K 5/057 (2006.01)
C07C 31/28 (2006.01)
C07C 29/70 (2006.01)
C08F 10/06 (2006.01)

(52) U.S. Cl.
CPC .............. *C08K 5/057* (2013.01); *C07C 29/70* (2013.01); *C07C 31/28* (2013.01); *C08F 10/06* (2013.01); *C07B 2200/13* (2013.01)

(58) Field of Classification Search
CPC ......... C08K 5/057; C07C 31/28; C07C 29/70; C07B 2200/13; C08F 10/06
See application file for complete search history.

(56) References Cited

U.S. PATENT DOCUMENTS

| 4,185,009 | A | 1/1980 | Idel et al. |
| 4,325,863 | A | 4/1982 | Hinsken et al. |
| 4,338,244 | A | 7/1982 | Hinsken et al. |
| 5,175,312 | A | 12/1992 | Dubs et al. |
| 5,216,052 | A | 6/1993 | Nesvadba et al. |
| 5,252,643 | A | 10/1993 | Nesvadba et al. |
| 5,367,044 | A | 11/1994 | Rosenquist |
| 5,475,123 | A | 12/1995 | Bos |
| 7,074,949 | B2* | 7/2006 | Bos ........................ C08K 5/057 525/515 |
| 2005/0222444 | A1 | 10/2005 | Bos |
| 2006/0173073 | A1* | 8/2006 | Taylor .................. A61K 31/315 514/494 |
| 2012/0190797 | A1 | 7/2012 | Kristiansen et al. |

FOREIGN PATENT DOCUMENTS

| DE | 25 00 092 A1 | 7/1976 |
| DE | 43 16 611 A1 | 11/1993 |
| DE | 43 16 622 A1 | 11/1993 |
| DE | 43 16 876 A1 | 11/1993 |
| DE | 42 40 313 A1 | 6/1994 |
| DE | 199 43 642 A1 | 3/2001 |
| EP | 0 589 839 A1 | 3/1994 |
| EP | 0 591 102 A1 | 4/1994 |
| EP | 1 291 384 A1 | 3/2003 |
| EP | 1 506 249 | 2/2005 |
| EP | 1 582 549 A1 | 10/2005 |
| WO | WO 02/26862 A1 | 4/2002 |
| WO | WO 03/095521 A1 | 11/2003 |

(Continued)

OTHER PUBLICATIONS

International Search Report dated Jul. 24, 2018 in PCT/EP2018/061201, citing documents AA, AC, BV and BW therein, 4 pages.
Streller, et al., "Isotactic Poly(propylene) Nanocomposites Based upon Boehmite Nanofillers", Macromolecular Materials and Engineering, vol. 293, Issue 3, Mar. 12, 2008, pp. 218-227.
Hambley, et al., "The crystal and Molecular Structure of Zinc(II) Monoglycerolate", Australian Journal of Chemistry, vol. 36, Jan. 1983, pp. 1249-1253.
Moezzi, et al., "Zinc Oxide Particles: Synthesis, Properties and Applications", Chemical Engineering Journal, vol. 185-186, Mar. 15, 2012, pp. 1-22.
Radoslovich, et al., "Crystalline Cobalt, Zinc, Manganese, and Iron Alkoxides of Glycerol", Australian Journal of Chemistry, vol. 23, Issue 10, 1970, pp. 1963-1971.
Slade, et al., "Crystal and Molecular Structure of Cobalt(II) Monoglycerolate", Acta Crystallographica Section B, vol. 27, Issue 12, Dec. 1971, pp. 2432-2436.

(Continued)

Primary Examiner — Robert D Harlan
(74) Attorney, Agent, or Firm — Grüneberg and Myers PLLC

(57) ABSTRACT

A method of manufacture of zinc monoglycerolate containing an incorporated modifier, and the product, the zinc monoglycerolate being in the form of agglomerates of crystallites, wherein the crystallite size based on the average coherence domain length is not more than 30 nm in the <100> direction, and not more than 60 nm in the <011> direction, as determined by the Scherrer equation via powder X-ray diffraction; and the aspect ratio computed by <100>/<011> coherent domain lengths is less than 0.65, preferably less than 0.56, in particular less than 0.44. Polymers containing this nucleating agent and methods for their production are also described. The zinc monoglycerolate is useful as a nucleating agent, and is very effective at low loading levels in polymers such as polypropylene.

20 Claims, 4 Drawing Sheets

(56) References Cited

FOREIGN PATENT DOCUMENTS

| | | |
|---|---|---|
| WO | WO 2005/113639 A1 | 12/2005 |
| WO | WO 2008/037364 A1 | 4/2008 |

OTHER PUBLICATIONS

U.S. Appl. No. 16/078,070, filed Aug. 21, 2018, US 2019-0300705 A1, Raphael Dabbous et al.
U.S. Appl. No. 16/348,259, filed May 8, 2019, US 2019-0316014 A1, Julio Albuerne et al.

* cited by examiner

NUCLEATING AGENTS, METHODS FOR THEIR PRODUCTION, AND ASSOCIATED POLYMER COMPOSITIONS

FIELD

The present invention relates to nucleating agents, methods for their production, and polymer compositions containing the nucleating agent.

BACKGROUND OF THE INVENTION

In the industrial processing of polyolefins by injection moulding, the degree of polymer crystallinity is generally controlled by use of appropriate levels of nucleating agents. These nucleating agents confer advantages to the polymer by raising the crystallisation temperature (Tc) of the polymer, increasing the crystallisation kinetics and, consequently, reducing the time taken to complete each cycle for the injection of an article (i.e. cycle time), which in turn increases output of the injection moulding equipment. Nucleating agents can also confer improved mechanical properties of the polymer body by virtue of the higher crystallinity obtained.

A feature that is becoming increasingly important is effectiveness at low loadings. Cost considerations are important in polymer products. If the cost of the nucleating agent required per kilogram of polymer is higher than the cost savings obtained from the associated raising of the crystallization temperature or reduction in the cycle time, then regardless of the efficacy of the nucleating agent, the nucleating agent will not be a commercial success. Accordingly, it is important to continually seek new or modified nucleating agents that have a high efficacy at low loadings over alternatives that have the same efficacy, but at higher loadings.

Nucleating agents that have been described or used in polyolefin manufacture include sorbitol-based compounds, cyclic dicarboxamides such as N,N'-dicyclohexyl-2,6-naphthalene dicarboxamide, cyclic dicarboxylate salts, aromatic heterocyclic phosphate salts, calcium malonate, and divalent metal propanetriolates such as zinc monoglycerolate.

Zinc monoglycerolate (ZMG) is an existing high-performance nucleating agent that has very good efficacy at low loadings (e.g. 500-1000 ppm) in commercial polyolefin production. The Zinc monoglycerolate was first synthesized, characterized and described by Taylor et al. (See Radoslovich, E. W., Raupach, M. R., Slade, P. G., & Taylor, R. M. (1970). Crystalline cobalt, zinc, manganese, and iron alkoxides of glycerol. *Australian Journal of Chemistry*, 23(10), 1963-1971; Hambley, T. W., & Snow, M. R. (1983) The crystal and molecular structure of zinc (II) monoglycerolate. *Australian Journal of Chemistry*, 36(6), 1249-1253; and Slade, P. G., Radoslovich, E. W., & Raupach, M. (1971) Crystal and molecular structure of cobalt (II) monoglycerolate. *Acta Crystallographica Section B: Structural Crystallography and Crystal Chemistry*, 27(12), 2432-2436.) The current commercial ZMG is produced based on the process described in U.S. Pat. No. 5,475,123 (1995) naming Bos as inventor, which is hereinafter called "unmodified ZMG". A second form of ZMG is also known from the patent literature—U.S. Pat. No. 7,074,949 also naming Bos as inventor (2006). In the method of the 2006 patent, zinc monoglycerolate is synthesized, either directly or indirectly, from hydrozincite ($Zn_5(CO_3)_2(OH)_6$). Hence, this material is referred to hereinafter as "hydrozincite-ZMG".

However, over time there are increased pressures on costs in polymer production, and it would be advantageous to develop new or modified nucleating agents that provide an even more favorable balance between the cost of the agent at the required loading levels and cost savings obtained during manufacturing of polymer products containing the agent at that loading level.

It is an object of the invention to provide a new or modified nucleating agent with an improved nucleating effect at low loadings, polymer compositions containing the nucleating agent and an associated method for the production of the nucleating agent.

SUMMARY

We have now found that we are able to produce a modified form of zinc monoglycerolate that provides an improved nucleating effect, particularly when compared to unmodified zinc monoglycerolate. The new form of zinc monoglycerolate is hereafter named "GMS-ZMG" (named after the glycerol monostearate (GMS) modifier predominately used), and provides a better nucleating effect than that achieved with more than twice the amount of unmodified zinc monoglycerolate. We produce this product (GMS-ZMG) using a new process of preparation.

According to one embodiment, there is provided a zinc monoglycerolate in the form of agglomerates of crystallites, wherein the crystallite size based on the average coherence domain length is not more than 30 nm in the <100> direction (i.e. along the <100> zone axis; hereafter often referred to as the <100> direction), and not more than 60 nm in the <011> direction, as determined by the Scherrer equation via powder X-ray diffraction. The product also suitably has an aspect ratio (measured or computed as <100>/<011> coherent domain lengths) of less than 0.65, for example less than 0.60 or less than 0.56. The aspect ratio in the preferred embodiments is less than 0.44.

Through the process described herein, the applicant has produced a form of zinc monoglycerolate that contains an incorporated modifier (e.g. GMS-ZMG), which results in the formation of agglomerates of crystallites, where the crystallites are extremely small. The agglomerates contain multiple crystallites, and are consequently significantly larger than the individual crystallites The applicant has conducted considerable research into ways to modify the zinc monoglycerolate in order to improve the efficiency of crystallization, through increasing the crystallization temperature and/or speeding up the time period to complete crystallization of the polymer.

The applicant achieved this result following many years of effort, during which a range of attempts were made to reduce the crystallite size of zinc monoglycerolate The applicant has now successfully achieved small crystal size of the zinc monoglycerolate through the use of a modifier and through the control of production conditions of the zinc monoglycerolate. The key innovation, as compared to prior art, is the ability to use the readily commercially available and relatively inexpensive "indirect or French process" zinc oxide (e.g. as obtainable from Umicore Zinc Chemicals) as the starting point, as opposed to hydrozincite (as described in U.S. Pat. No. 7,074,949). For a description of the "indirect or French process" for zinc oxide production, see Moezzi, A., McDonagh, A. M., & Cortie, M. B. (2012) Zinc oxide particles: Synthesis, properties and applications. *Chemical Engineering Journal*, 185, 1-22. The modifier does not alter the fundamental chemical structure of zinc monoglycerolate.

According to one embodiment, there is provided a process for the preparation of zinc monoglycerolate, comprising reacting a zinc compound, which is different from hydrozincite (i.e. it is a zinc compound other than hydrozincite, and is not derived from hydrozincite), with glycerol and a modifier, in the presence of an acid catalyst, wherein:

the zinc compound is selected from the group consisting of zinc oxide, zinc carbonate, zinc hydroxide, zinc carboxylate and combinations thereof, or/and the reaction is conducted in the presence of less than 10% by weight water, based on the total weight of the reaction composition.

In preferred embodiments, both conditions are used in the process.

The present application also describes preferred temperature conditions for the production of zinc monoglycerolate from zinc oxide and glycerol, in the presence of an acid catalyst and a modifier, to control the crystallite and agglomerate size of the product.

By producing zinc monoglycerolate in the specified modified form described above, the applicant has been able to produce polymer compositions containing the zinc monoglycerolate (nucleating agent) (GMS-ZMG), in which the polymer compositions have a relatively high crystallization temperature at a low loading of the zinc monoglycerolate.

Thus, according to a further embodiment, there is provided a composition comprising an organic polymer and the zinc monoglycerolate described above. The zinc glycerolate may be present in an amount of from 0.01% to 20% by weight of the polymeric composition.

According to another embodiment, there is provided a composition comprising an organic polymer and a nucleating agent comprising zinc monoglycerolate, wherein the zinc monoglycerolate has a crystallite size based on the average coherence domain length of not more than 30 nm in the <100> direction, and not more than 60 nm in the <011> direction, as determined by the Scherrer equation via powder X-ray diffraction; and the ratio of the above coherent domain lengths (which may be referred to as the aspect ratio) is less than 0.65, for example less than 0.60 or less than 0.56, preferably less than 0.44. Having an aspect ratio within this range indicates that the stack height of the zinc glycerol platelets is smaller than their sheet length.

The present application provides for the use of the zinc monoglycerolate of the type described above (GMS-ZMG) as a nucleating agent. Also provided is the use of the zinc monoglycerolate of the type described above (GMS-ZMG) to improve (increase) the crystallisation temperature of an organic polymer. This may be by way of increasing the crystallisation temperature of an organic polymer at low loading, e.g. 400 ppm or less.

DETAILED DESCRIPTION

Figure 1:
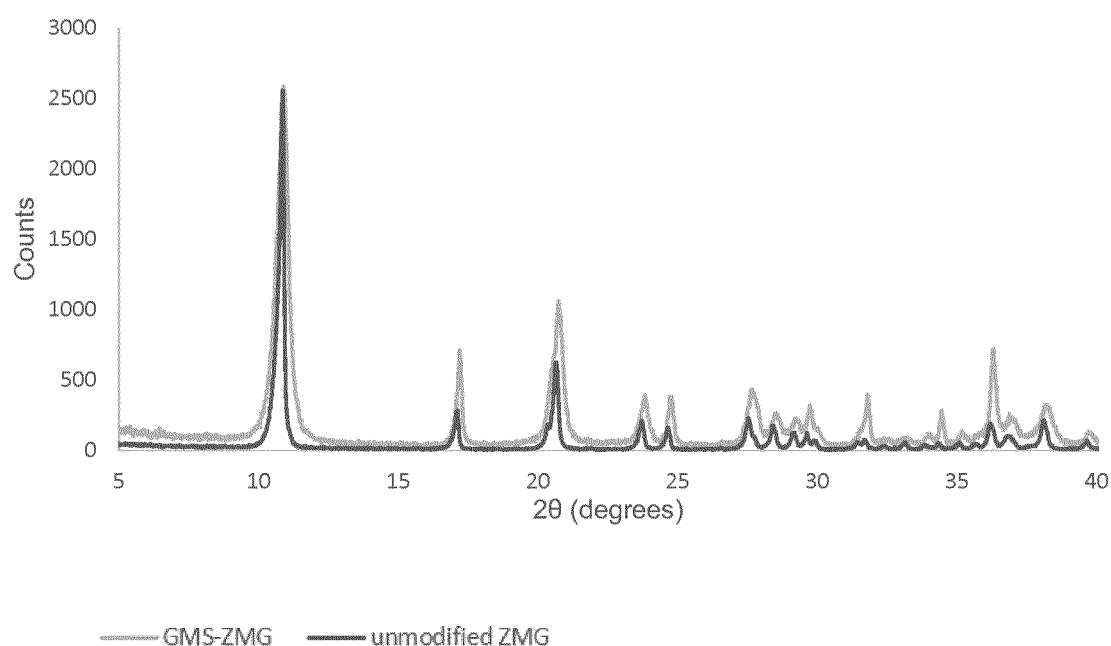
FIG. 1 shows the XRD pattern of modified zinc monoglycerolate according to the embodiment of the present invention (GMS-ZMG). Also shown is the XRD pattern of unmodified ZMG. The X-axis shows 2θ (in degrees), and the Y-axis shows the counts (peak intensity). The peak at 2θ=10.9° is the (100) peak of zinc monoglycerolate. Both XRD patterns have been normalized such that the (100) peak has the same intensity. The (100) peak of GMS-ZMG is broader than in unmodified ZMG, i.e. GMS-ZMG crystallites are smaller.

The zinc monoglycerolate, method of manufacture, polymer compositions and uses according to particular embodiments of the invention are described below.

Prior to outlining the details of the method of production of the modified zinc monoglycerolate, notable features of the modified zinc monoglycerolate will be described. The modified zinc monoglycerolate is useful as a nucleating agent. Accordingly, references to zinc monoglycerolate may be used interchangeably with "nucleating agent".

The zinc monoglycerolate (GMS-ZMG) is preferably at least 90% by weight zinc monoglycerolate (the chemical compound). The modifier is preferably not more than 5 mol % of the zinc monoglycerolate content. The modifier is incorporated in a manner such that it is not simply an admixture of the modifier with pre-prepared unmodified zinc monoglycerolate. The modifier is added during the production of the zinc monoglycerolate. It has been found that the modified material is crystal-structurally ZMG (X-Ray Diffraction evidence). In the preferred embodiment, the modifier, glycerol monostearate, was used at 5.47 wt % of total GMS-ZMG mass.

The modifier is an agent that is capable of modifying the crystallite size of the zinc monoglycerolate during manufacture. A suitable class of agents found to have such modifying capabilities are the glycerol carboxylate esters. The glycerol carboxylate is preferably a monoglycerolate of an acid, or a monoacylglycerol. The acid is preferably a saturated fatty acid, and may be a C6 to C24 saturated fatty acid. According to preferred embodiments, the modifier is glycerol monostearate (ester of stearic acid). It is noted that mere fatty acid triglycerides, e.g. coconut oil, are not effective as modifiers, so the presence of two hydroxyl groups in the glycerol ester is preferred.

The zinc monoglycerolate of the present application (GMS-ZMG) containing incorporated modifier is in the form of agglomerates of crystallites. The agglomerate size can be measured by scanning electron microscopy (SEM). Using SEM, a suitable procedure involves adhering the zinc monoglycerolate material to double sided carbon tape. The tape is attached to the SEM mount (and loose material is blown away by compressed nitrogen). The adhered zinc monoglycerolate material is then sputter-coated with a metal (for example, platinum); and images are acquired in a Scanning Electron Microscope (SEM) at various magnifications. This technique ensures that the measured agglomerate size distribution for the zinc monoglycerolate material is consistent with the agglomerate size distribution of the loose product (i.e. no further processing in suspension medium, etc.). The size of each particle (as a diameter) is calculated for the visible agglomerates within the image area. The agglomerate size is hard to measure without being unaffected by processing conditions, and the notion of agglomerate size is too vague to be of universal usefulness.

Consequently, the agglomerate sizes used in this document are not provided normatively, but are instead given as descriptions indicative of successful synthesis (loose large agglomerates comprising small crystallites).

The agglomerates comprise multiple crystallites. The agglomerates that show prominently in Scanning Electron Microscopy (SEM) images are typically between 5 μm and 50 μm wide. It is advantageous to have multiple crystallites agglomerated into micron-sized particles, particularly micron-sized particles in which the agglomerates are loosely bound. Presenting the material as discrete sub 100 nanometer-sized particles gives rise to handling difficulties and concerns with packaging and transport of the material. Agglomerates that are in the micron size range avoid these problems. Whilst agglomeration is thus attractive, it is important that the nature of the agglomerates does not lead to difficulties in the individual crystallites separating and spreading through the polymer composition. The techniques described herein for the production of the GMS modified zinc monoglycerolate (GMS-ZMG) are believed to provide agglomerates that are loosely held.

The zinc monoglycerolate of the present application (GMS-ZMG) has very small crystallite (as determined by XRD), and hence delivers more crystallites (i.e. active nucleating agent centers) per unit mass, which disperse effectively.

The zinc monoglycerolate of the present application (GMS-ZMG) raises the crystallization temperature, even when used in low amounts.

XRD patterns are acquired by means of an X-Ray diffraction instrument set up according to the Bragg-Brentano ($\theta$-$2\theta$) geometry, scanning between the desired $2\theta$ values. Each peak corresponds to a set of lattice planes described by a Miller index, e.g. (100). For a given peak, e.g. the (100) peak, the width of the peak corresponds to the average coherence domain length (i.e. the crystallite size), in the direction of that zone axis, i.e. the <100> in this example, measured using the full width at half maximum (FWHM) of the (100) peak. The Scherrer equation can then be used to calculate crystallite size:

$$\tau = K\lambda/\beta \cos \theta;$$

where $\tau$ is the mean crystallite size (nm), K is the dimensionless shape factor (taken here to be 0.9; the same $\beta$ must be used for all data that are mutually compared), $\lambda$ is the wavelength of the X-ray used (0.154 nm (i.e. Cu K$\alpha$ radiation)), $\beta$ is the line broadening at FWHM expressed in radians, and $\theta$ is the Bragg angle (expressed in degrees; (2$\theta$ value of peak)/2). Line broadening is assumed to be from coherence domain length changes alone.

The zinc monoglycerolate (GMS-ZMG) can be produced with a crystallite size in the <100> direction (determined by the above method) of between 10 and 30 nm, between 10 and 25 nm, or between 10 and 20 nm. The mean crystallite size is typically less than 25 nm, less than 22 nm, or less than 20 nm.

The zinc monoglycerolate can be produced with a crystallite size in the <011> direction (determined by the above method) of between 20 and 50 nm, between 20 and 48 nm, or between 20 and 46 nm.

The crystallite size of GMS-ZMG is not more than 30 nm in the <100> direction (i.e. coherence domain length along the stacking direction), and not more than 60 nm in the <011> direction (i.e. coherence domain length along the planar direction), as determined by the Scherrer equation via powder X-ray diffraction. The crystallite size in the <011> direction is preferably less than 60 nm. The ratio of the above coherent domain lengths (aspect ratio) is suitably approximately half, or more precisely, less than 0.65, for example less than 0.60 or less than 0.56, preferably less than 0.44.

The temperature is preferably kept below 120° C. for the duration of the reaction. However, taking the temperature above 120° C. for a short duration should not result in such processes falling outside the scope of the present application. The time period during which the reaction is above 120° C. is preferably not more than 10% of the total duration of the reaction. The temperature is preferably raised during the reaction to reach a peak that is between 100° C. and 120° C. Prior art processes have involved higher temperature reaction, or more prolonged time periods above 100° C. As a consequence of the different temperature conditions during the reaction (at least in part), the mean crystallite size of the product produced under the prior art conditions has been above the ranges indicated for the product of the present application.

The zinc compound may be selected from the group consisting of zinc oxide, zinc carbonate, zinc hydroxide, zinc carboxylate and combinations thereof. However, the novelty of this invention pertains to its ability to use the readily available indirect or French process zinc oxide to produce to highly dispersible nucleating agents (more dispersible than afforded by the prior art). Moreover, it is noted that zinc oxide used herein excludes zinc oxide that has been formed from hydrozincite, and indeed excludes the use of hydrozincite itself (hydrozincite-ZMG), which was described in Bos 2006. The use of hydrozincite, via the stipulated method of Bos 2006, tends to result in larger crystallite sizes than those specified in the present application (particularly when combined with other processing conditions), and is therefore preferably not used.

The amount of glycerol in the reaction composition is preferably between 95 and 110 mol %. The amount is preferably between 98% and 105 mol %, and is typically used in a stoichiometric amount.

In terms of the modifier amount, this modifier amount is preferably between 1.0 and 5.0 mol %. Using a lower amount tends to result larger mean crystallite size, although other factors also impact on the crystallite size achieved. The modifier contributes to a smaller mean crystallite size when incorporated at a high enough level. The level is preferably at least 1.0 mol %, more preferably greater than 1.7, 1.9, 2.0, 2.1, 2.2 or 2.3 mol %. The range of 2.0 to 5.0 mol % is particularly suited. The ideal amount used may be around 2.5 mol %. Higher amounts can also be used, however it is found that no further benefit is achieved when increasing the level to at/above 5.0 mol %, and levels at/above this can also adversely impact process-ability.

A preferred preparation method of the zinc monoglycerolate according to the present invention comprises combining the zinc compound, modifier and between 75% and 95% by weight of the total glycerol, mixing, and subsequently adding a combination of the balance of the glycerol, acetic acid and water.

The reaction is conducted in the presence of an acid catalyst. The catalyst is preferably an acid or acid salt such as a lower alkyl carboxylic acid (e.g. C2 to C6 carboxylic acid), such as acetic acid, valeric acid; a poly-carboxylic acid such as citric acid, malic acid, maleic acid, succinic acid, malonic acid, hippuric acid, tartaric acid, oxalic acid; a medium/long chain acid such as lauric acid, stearic acid; any other acid such as levulinic acid, benzoic acid, boric acid, trifluoroacetic acid; or mixtures thereof.

The catalyst may also be a zinc salt of any of the said acids, for example zinc acetate; though in the preferred embodiment the acid is added, in situ, to the zinc oxide.

The amount of catalyst used is preferably between 0.2 and 5 mol % with respect to the zinc compound.

One key preferred feature in the process for the preparation of the modified zinc monoglycerolate is the water content in the reaction composition. The water content is preferably quite low. The water content is preferably not more than 10%, preferably not more than 8%, 6%, 4% or 2% of the total reaction composition by weight. There may be a low amount of water present in the acid catalyst composition, since acids are commonly available in aqueous solutions. Water as impurity in glycerol can be tolerated. Water is generated in the reaction, but only the presence of a significant quantity of water in the reaction composition at the outset seems to contribute to undesirably large crystallite sizes.

A further aspect of the invention relates to a polymer composition comprising an organic polymer (at least one) and from 0.001% to 20%, for example 0.01% to 20%, 0.001% to 10%, 0.001% to 5% or 0.01% to 1%, by weight (based on the polymeric composition) of the zinc monoglycerolate (GMS-ZMG) as described above.

Examples of organic polymers are:

1. Polymers of monoolefins and diolefins, for example polypropylene, polyisobutylene, polybut-1-ene, poly-4-methylpent-1-ene, polyvinylcyclohexane, polyisoprene or poly-butadiene, polyhexene, polyoctene, as well as polymers of cycloolefins, for instance of cyclopentene, cyclohexene, cyclooctene or nor-bornene, polyethylene (which optionally can be crosslinked), for example high density polyethylene (HDPE), high density and high molecular weight polyethylene (HDPE-HMW), high density and ultra-high molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:
a) radical polymerisation (normally under high pressure and at elevated temperature).
b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (Du-Pont), metallocene or single-site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), very low density polyethylene, propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example C5-C9) including hydrogenated modifications thereof (e.g. tackifiers) and mixtures of polyalkylenes and starch.

Homopolymers and copolymers from 1.)-4.) may have any stereostructure including syndiotactic, isotactic, hemi-isotactic or atactic; where atactic polymers are preferred. Stereoblock polymers are also included. Copolymers from 1.)-4.) may by random or block-copolymers, homo- or heterophasic, or High Crystalline Homopolymer.

5. Polystyrene, poly(p-methylstyrene), poly(α-methylstyrene).

6. Aromatic homopolymers and copolymers derived from vinyl aromatic monomers including styrene, α-methylstyrene, all isomers of vinyl toluene, especially p-vinyltoluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.

6a. Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/isoprene/butadiene/styrene, styrene/ethylene/butylene/styrene or styrene/ethylene/propylene/styrene, HIPS, ABS, ASA, AES.

6b. Hydrogenated aromatic polymers derived from hydrogenation of polymers mentioned under 6.), especially including polycyclohexylethylene (PCHE) prepared by hydrogenating atactic polystyrene, often referred to as polyvinylcyclohexane (PVCH).

6c. Hydrogenated aromatic polymers derived from hydrogenation of polymers mentioned under 6a.).

Homopolymers and copolymers may have any stereostructure including syndiotactic, isotactic, hemi-isotactic or atactic; where atactic polymers are preferred. Stereoblock polymers are also included.

7. Graft copolymers of vinyl aromatic monomers such as styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers. Polyvinyl chloride may be rigid or flexible (plasticized).

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or poly-butadienes on the one hand and aliphatic or aromatic polyisocyanates on the other, as well as precursors thereof. Polyurethanes formed by the reaction of: (1) diisocyanates with short-chain diols (chain extenders) and (2) diisocyanates with long-chain diols (thermoplastic polyurethanes, TPU).

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems). The polyamides may be amorphous.

17. Polyureas, polyimides, polyamideimides, polyetherimides, polyesterimides, polyhydantoins and polybenzimidazoles.

18. Polyesters derived from dicarboxylic acids and diols and/or from hydroxycarboxylic acids or the corresponding lactones or lactides, for example polyethylene terephthalate, polybutylene terephthalate, poly-1,4-dimethylolcyclohexane terephthalate, polypropylene terephthalate, polyalkylene naphthalate and polyhydroxybenzoates as well as copolyether esters derived from hydroxyl-terminated polyethers, and also polyesters modified with polycarbonates or MBS. Copolyesters may comprise, for example—but are not limited to—polybutyl-enesuccinate/terephtalate, polybutyleneadipate/terephthalate, polytetramethyleneadipate/terephthalate, polybutylensuccinate/adipate, polybutylensuccinate/carbonate, poly-3-hydroxybutyrate/octanoate copolymer, poly-3-hydroxybutyrate/hexanoate/decanoate terpolymer. Furthermore, aliphatic polyesters may comprise, for example—but are not limited to—the class of poly (hydroxyalkanoates), in particular, poly(propiolactone), poly(butyrolactone), poly(pivalolactone), poly(valerolactone) and poly(caprolactone), polyethylenesuccinate, polypropylenesuccinate, polybutylenesuccinate, polyhexamethylenesuccinate, polyethyleneadipate, polypropyleneadipate, polybutyleneadipate, polyhexamethyleneadipate, polyethyleneoxalate, polypropyleneoxalate, polybutyleneoxalate, polyhexamethyleneoxalate, polyethylenesebacate, polypropylenesebacate, polybutylenesebacate, polyethylene furanoate and polylactic acid (PLA) as well as corresponding polyesters modified with polycarbonates or MBS. The term "polylactic acid (PLA)" designates a homo-polymer of preferably poly-L-lactide and any of its blends or alloys with other polymers; a co-polymer of lactic acid or lactide with other monomers, such as hydroxy-carboxylic acids, like for example glycolic acid, 3-hydroxy-butyric acid, 4-hydroxy-butyric acid, 4-hydroxy-valeric acid, 5-hydroxy-valeric acid, 6-hydroxy-caproic acid and cyclic forms thereof; the terms "lactic acid" or "lactide" include L-lactic acid, D-lactic acid, mixtures and dimers thereof, i.e. L-lactide, D-lactide, meso-lactide and any mixtures thereof. Preferred polyesters are PET, PET-G, PBT.

19. Polycarbonates and polyester carbonates. The polycarbonates are preferably prepared by reaction of bisphenol compounds with carbonic acid compounds, in particular phosgene or, in the melt transesterification process, diphenyl carbonate or dimethyl carbonate. Homopolycarbonates based on bisphenol A and copolycarbonates based on the monomers bisphenol A and 1,1-bis-(4-hydroxyphenyl)-3,3,5-trimethylcyclohexane (bisphenol TMC) are particularly preferred. These and further bisphenol and diol compounds which can be used for the polycarbonate synthesis are disclosed inter alia in WO08037364 (p. 7, line 21 to p. 10, line 5), EP1582549 ([0018] to [0034]), WO02026862 (p. 2, line 23 to p. 5, line 15), WO05113639 (p. 2, line 1 to p. 7, line 20). The polycarbonates can be linear or branched. Mixtures of branched and unbranched polycarbonates can also be used. Suitable branching agents for polycarbonates are known from the literature and are described, for example, in patent specifications U.S. Pat. No. 4,185,009 and DE2500092 (3,3-bis-(4-hydroxyaryl-oxindoles according to the invention, see whole document in each case), DE4240313 (see p. 3, line 33 to 55), DE19943642 (see p. 5, line 25 to 34) and U.S. Pat. No. 5,367,044 as well as in literature cited therein. The polycarbonates used can additionally be intrinsically branched, no branching agent being added here within the context of the polycarbonate preparation. An example of intrinsic branchings are so-called Fries structures, as are disclosed for melt polycarbonates in EP1506249. Chain terminators can additionally be used in the polycarbonate preparation. Phenols such as phenol, alkylphenols such as cresol and 4-tert-butylphenol, chlorophenol, bromophenol, cumylphenol or mixtures thereof are preferably used as chain terminators. Polyester carbonates are obtained by reaction of the bisphenols already mentioned, at least one aromatic dicarboxylic acid and optionally carbonic acid equivalents. Suitable aromatic dicarboxylic acids are, for example, phthalic acid, terephthalic acid, isophthalic acid, 3,3'- or 4,4'-diphenyldicarboxylic acid and benzophenone-dicarboxylic acids. A portion, up to 80 mol-%, preferably from 20 to 50 mol-%, of the carbonate groups in the polycarbonates can be replaced by aromatic dicarboxylic acid ester groups.

20. Polyketones.
21. Polysulfones, polyether sulfones and polyether ketones.
22. Crosslinked polymers derived from aldehydes on the one hand and phenols, ureas and melamines on the other hand, such as phenol/formaldehyde resins, urea/formaldehyde resins and melamine/formaldehyde resins.
23. Drying and non-drying alkyd resins.
24. Unsaturated polyester resins derived from copolyesters of saturated and unsaturated dicarboxylic acids with polyhydric alcohols and vinyl compounds as crosslinking agents, and also halogen-containing modifications thereof of low flammability.
25. Crosslinkable acrylic resins derived from substituted acrylates, for example epoxy acrylates, urethane acrylates or polyester acrylates.
26. Alkyd resins, polyester resins and acrylate resins crosslinked with melamine res-ins, urea resins, isocyanates, isocyanurates, polyisocyanates or epoxy resins.
27. Crosslinked epoxy resins derived from aliphatic, cycloaliphatic, heterocyclic or aromatic glycidyl compounds, e.g. products of diglycidyl ethers of bisphenol A, bisphenol E and bisphenol F, which are crosslinked with customary hardeners such as anhydrides or amines, with or without accelerators.
28. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
29. Blends of the aforementioned polymers (polyblends), for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and co-polymers, PA/HDPE, PA/PP, PA/PPO, PBT/PC/ABS or PBT/PET/PC.
30. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.
31. Aqueous emulsions of natural or synthetic rubber, e.g. natural latex or lattices of carboxylated styrene/butadiene copolymers.
32. Adhesives, for example block copolymers such as SIS, SBS, SEBS, SEPS (S represents styrene, I isoprene, B polybutadiene, EB ethylene/butylene block, EP polyethylene/polypropylene block).
33. Rubbers, for example polymers of conjugated dienes, e.g. polybutadiene or polyisoprene, copolymers of mono- and diolefins with one another or with other vinyl monomers, copolymers of styrene or α-methylstyrene with dienes or with acrylic derivatives, chlorinated rubbers, natural rubber.
34. Elastomers, for example Natural polyisoprene (cis-1,4-polyisoprene natural rubber (NR) and trans-1,4-polyisoprene gutta-percha), Synthetic polyisoprene (IR for isoprene rubber), Polybutadiene (BR for butadiene rubber), Chloroprene rubber (CR), polychloroprene, Neoprene, Baypren etc., Butyl rubber (copolymer of isobutylene and isoprene, IIR), Halogenated butyl rubbers (chloro butyl rubber: CIIR; bromo butyl rubber: BIIR), Styrene-butadiene Rubber (copolymer of styrene and butadiene, SBR), Nitrile rubber (copolymer of butadiene and acrylonitrile, NBR), also called Buna N rubbers Hydrogenated Nitrile Rubbers (HNBR) Therban and Zetpol, EPM (ethylene propylene rubber, a copolymer of ethylene and propylene) and EPDM rubber (ethylene propylene diene rubber, a terpolymer of ethylene, propylene and a diene-component), Epichlorohydrin rubber (ECO), Polyacrylic rubber (ACM, ABR), Silicone rubber (SI, Q, VMQ), Fluorosilicone Rubber (FVMQ), Fluoroelastomers (FKM, and FEPM) Viton, Tecnoflon, Fluorel, Aflas and Dai-El, Perfluoroelastomers (FFKM) Tecnoflon PFR, Kalrez, Chemraz, Perlast, Polyether block amides (PEBA), Chlorosulfonated polyethylene (CSM), (Hypelon), Ethylene-vinyl acetate (EVA), Thermoplastic elastomers (TPE), The proteins resilin and elastin, Polysulfide rubber, Elastolefin, elastic fiber used in fabric production.
35. Thermoplastic elastomers, for example Styrenic block copolymers (TPE-s), Thermoplastic olefins (TPE-o), Elastomeric alloys (TPE-v or TPV), Thermoplastic polyurethanes (TPU), Thermoplastic copolyester, Thermoplastic polyamides, Reactor TPO's (R-TPO's), Polyolefin Plastomers (POP's), Polyolefin Elastomers (POE's).

The preferred organic polymers may be selected from the group consisting of polyolefins (such as polyethylene, polypropylene, and so forth), polyvinyl chloride, polystyrene, polyacrylamide, polyester, polyamide copolymers thereof, and copolymers of one or more of acrylonitrile, butadiene and styrene with each other or with another comonomer. Polyolefins are preferred, and polypropylene is particularly preferred. The polymer may be processed into polymeric articles such as fibres, films, fabrics, packaging or coatings.

The zinc monoglycerolate containing incorporated modifier (GMS-ZMG) is typically present in amounts of from approximately 0.01 to 20% by weight based on the total weight of the polymeric blend. In the final plastic product the concentration is generally in the range of 0.01 to 2% but masterbatch composition for preparation of the product may contain up to 20% by weight. The organic polymer may be present in amounts of approximately 80% to 99.99% by weight based on the total weight of the polymeric blend.

The amount of GMS modified zinc monoglycerolate (GMS-ZMG) in the polymer is preferably not more than 400 ppm, and may even be 380 ppm or less, 360 ppm or less, 340 ppm or less, 320 ppm or less, or 300 ppm or less. The amount may be as low as 100 ppm, or 50 ppm, or less.

About 200 ppm+/−100 ppm, or +/−50 ppm is a suitable target amount. Typical amounts of conventional nucleating agents (e.g. unmodified ZMG) in isotactic polypropylene are generally 500 ppm or more, so this reduced amount represents a significant cost savings, while not adversely impacting on the crystallization timing achieved.

The polymeric composition may further include conventional compounding ingredients in minor amounts, for example 0.001 to 20%, preferably 0.005% to 5%, relative to the weight of the polymeric composition.

Examples of conventional compounding ingredients are:
1. Antioxidants
1.1. Alkylated monophenols, for example 2,6-di-tert-butyl-4-methylphenol, 2-tert-butyl-4,6-dimethyl phenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexyl phenol, 2,6-di-tert-butyl-4-methoxymethylphenol, nonylphenols which are linear or branched in the side chains, for example, 2,6-di-nonyl-4-methylphenol, 2,4-dimethyl-6-(1'-methyl undec-1'-yl)phenol, 2,4-dimethyl-6-(1'-methyl heptadec-1'-yl)phenol, 2,4-dimethyl-6-(1'-methyltridec-1'-yl) phenol and mixtures thereof.
1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.
1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl) adipate.
1.4. Tocopherols, for example α-tocopherol, β-tocopherol, γ-tocopherol, δ-tocopherol and mixtures thereof (vitamin E).
1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl) disulfide.
1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethyl benzyl)-4-nonylphenol], 4,4'-methylenebis(2,6-tert-butyl phenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra-(5-tert-butyl-4-hydroxy-2-methylphenyl)pentane.
1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.
1.8. Hydroxybenzylated malonates, for example dioctadecyl-2,2-bis(3,5-di-tert-butyl-2-hydroxybenzyl)malonate, di-octadecyl-2-(3-tert-butyl-4-hydroxy-5-methylbenzyl)malonate, di-dodecylmercaptoethyl-2,2-bis(3,5-di-tert-butyl-4-hydroxybenzyl) malonate, bis[4-(1,1,3,3-tetramethylbutyl) phenyl]-2,2-bis(3,5-di-tert-butyl-4-hydroxybenzyl) malonate.
1.9. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.
1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.
1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.
1.12. Acylaminophenols, for example 4-hydroxylauranilide, 4-hydroxystearanilide, octyl N-(3,5-ditert-butyl-4-hydroxyphenyl)carbamate.
1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N, N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane; 3,9-bis[2-{3-(3-tert-butyl-4-hydroxy-5-methylphenyl)propionyloxy}-1,1-dimethylethyl]-2,4,8,10-tetraoxaspiro[5.5]undecane.

1.15. Esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl)propionic acid e.g. N,N'-bis(3,5-di-tert-butyl-4-hydroxyphenylpropionyl)hexamethylenediamide, N,N'-bis(3,5-di-tert-butyl-4-hydroxy-phenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard®XL1, supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino] ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octyl-phenothiazines, N-allylphenothiazine, N,N,N',N'-tetraphenyl-1,4-diaminobut-2-ene.

2. UV absorbers and light stabilizers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetra methyl butyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl) benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl) phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl) phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl) benzotriazole, 2-(3'-dodecyl-2'-hydroxy-5'-methyl phenyl) benzotriazole, 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300;

where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)-phenyl]benzotriazole; 2-[2'-hydroxy-3'-(1,1,3,3-tetramethylbutyl)-5'-(α,α-dimethylbenzyl)-phenyl] benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butyl-phenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate, N-(β-carbomethoxy-β-cyanovinyl)-2-methylindoline, neopentyl tetra(α-cyano-β,β-diphenylacrylate.

2.5. Nickel compounds, for example nickel complexes of 2,2'-thio-bis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenylundecylketoxime, nickel complexes of 1-phenyl-4-lauroyl-5-hydroxypyrazole, with or without additional ligands.

2.6. Sterically hindered amines, for example carbonic acid bis(1-undecyloxy-2,2,6,6-tetramethyl-4-piperidyl)ester, bis (2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butanetetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensate of N,N'-bis(2,2,6,6-tetramethyl-4-piperidyl)hexamethylenediamine and 4-cyclohexylamino-2,6-dichloro-1,3,5-triazine, a condensate of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2,6,6-tetramethylpiperidine (CAS Reg. No. [192268-64-7]); N-(2,2,6,6-tetramethyl-4-piperidyl)-n-dodecylsuccinimide, N-(1,2,2,6,6-pentamethyl-4-piperidyl)n-dodecylsuccinimide, 2-undecyl-7,7,9,9-tetramethyl-1-oxa-3,8-diaza-4-oxospiro[4,5]decane, a reaction product of 7,7,9,9-tetramethyl-2-cycloundecyl-1-oxa-3,8-diaza-4-oxospiro-[4,5]decane and epichlorohydrin, 1,1-bis(1,2,2,6,6-pentamethyl-4-piperidyloxycarbonyl)-2-(4-methoxyphenyl)ethene, N,N'-bisformyl-N,N'-bis(2,2,6,6-tetramethyl-4-piperidyl)hexamethylenediamine, a diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-α-olefin copolymer with 2,2,6,6-tetramethyl-4-aminopiperidine or 1,2,2,6,6-pentamethyl-4-aminopiperidine, 2,4-bis[N-(1-cyclohexyloxy-2,2,6,6-tetramethylpiperidine-4-yl)-N-butylamino]-6-(2-hydroxyethyl)amino-1,3,5-triazine, 1-(2-hydroxy-2-methylpropoxy)-4-octadecanoyloxy-2,2,6,6-tetramethylpiperidine, 5-(2-ethylhexanoyl)oxymethyl-3,3,5-trimethyl-2-morpholinone, Sanduvor (Clariant; CAS Reg. No. 106917-31-1], 5-(2-ethylhexanoyl)oxymethyl-3,3,5-trimethyl-2-morpholinone, the reaction product of 2,4-bis[(1-cyclohexyloxy-2,2,6-piperidine-4-yl)butylamino]-6-chloro-s-triazine with N,N'-bis(3-aminopropyl) ethylenediamine), 1,3,5-tris(N-cyclohexyl-N-(2,2,6,6-tetramethylpiperazine-3-one-4-yl)amino)-s-triazine, 1,3,5-tris(N-cyclohexyl-N-(1,2,2,6,6-pentamethylpiperazine-3-one-4-yl)amino)-s-triazine,

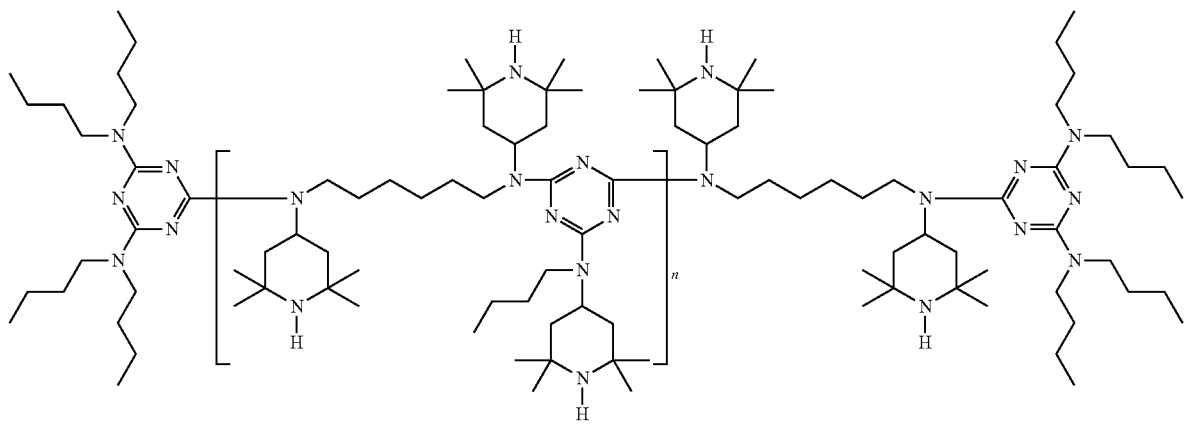

(Chimassorb®2020)

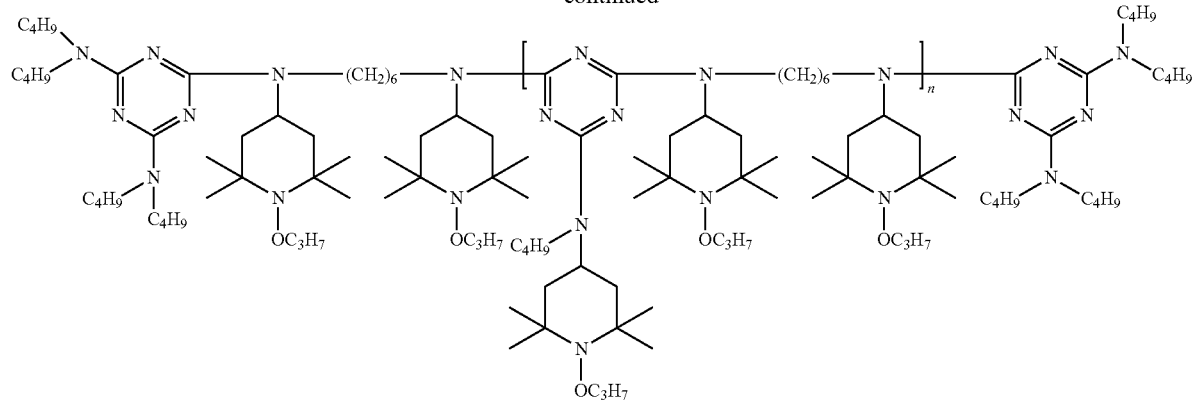

(Tinuvin®NOR 371)

1,3,5-Triazine-2,4,6-triamine, N,N'''-1,6-hexanediylbis[N',N''-dibutyl-N,N',N''-tris(2,2,6,6-tetramethyl-4-piperidinyl)- reaction products with 3-bromo-1-propene, oxidized, hydrogenated, 1,3,5-Triazine-2,4,6-triamine, N,N'''-1,6-hexanediylbis[N',N''-dibutyl-N,N',N''-tris(2,2,6,6-tetramethyl-4-piperidinyl)- and combinations thereof.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-di methylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine, 2,4-bis(4-[2-ethylhexyloxy]-2-hydroxyphenyl)-6-(4-methoxyphenyl)-1,3,5-triazine, 2-(4,6-bis-biphenyl-4-yl-1,3,5-triazin-2-yl)-5-(2-ethyl-(n)-hexyloxy)phenol.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearylpentaerythritol diphosphite, tris(2,4-di-tert-butylphenyl) phosphite, diisodecyl pentaerythritol diphosphite, bis(2,4-di-tert-butylphenyl)pentaerythritol diphosphite, bis(2,4-di-cumylphenyl)pentaerythritol diphosphite, bis(2,6-di-tert-butyl-4-methylphenyl)pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 6-fluoro-2,4,8,10-tetra-tertbutyl-12-methyl-dibenz[d,g]-1,3,2-dioxaphosphocin, 2,2',2''-nitrilo[triethyltris(3,3',5,5'-tetra-tertbutyl-1,1'-biphenyl-2,2'-diyl) phosphite], 2-ethylhexyl(3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane, phosphorous acid, mixed 2,4-bis(1,1-dimethylpropyl)phenyl and 4-(1,1-dimethylpropyl)phenyl triesters (CAS No. 939402-02-5), Phosphorous acid, triphenyl ester, polymer with alpha-hydro-omega-hydroxypoly[oxy(methyl-1,2-ethanediyl)], C10-16 alkyl esters (CAS No. 1227937-46-3).

The following phosphites are especially preferred:
Tris(2,4-di-tert-butylphenyl) phosphite (Irgafos® 168, Ciba Specialty Chemicals Inc.), tris(nonylphenyl) phosphite,

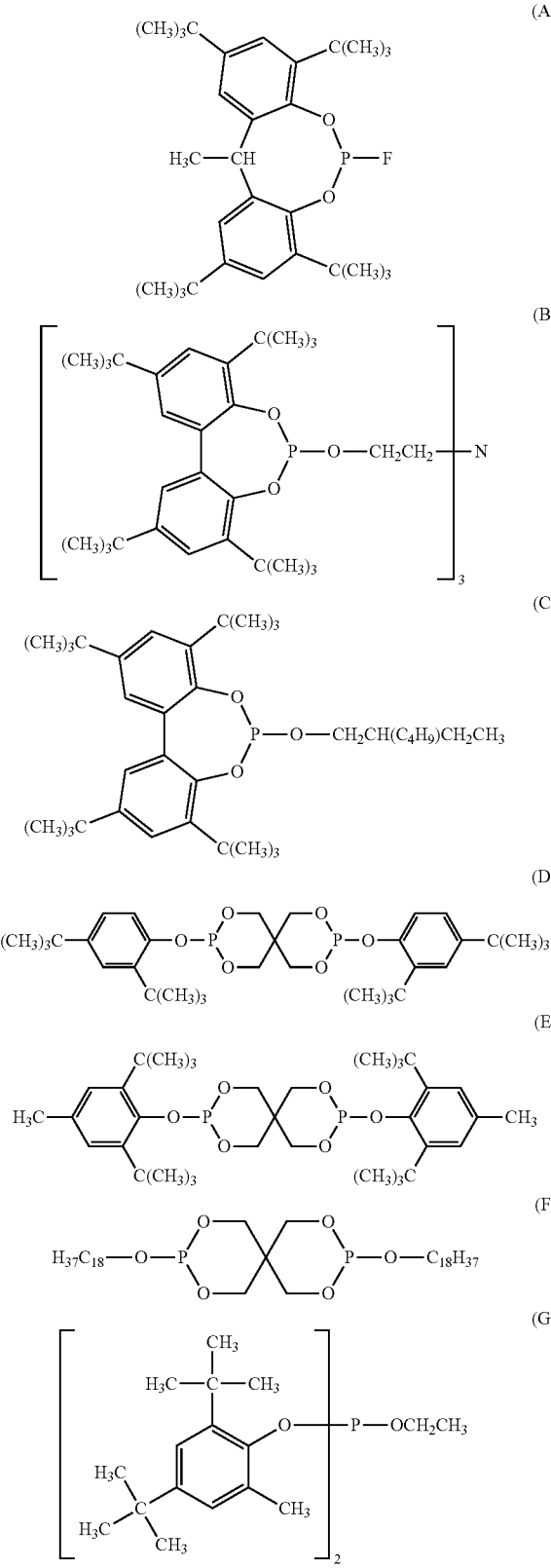

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenylnitrone, N-ethyl-alpha-methylnitrone, N-octyl-alpha-heptylnitrone, N-lauryl-alpha-undecylnitrone, N-tetradecyl-alpha-tridecylnnitrone, N-hexadecyl-alpha-pentadecylnitrone, N-octadecyl-alpha-heptadecylnitrone, N-hexadecyl-alpha-heptadecylnitrone, N-ocatadecyl-alpha-pentadecylnitrone, N-heptadecyl-alpha-heptadecylnitrone, Noctadecyl-alpha-hexadecylnitrone, nitrone derived from N,N-dialkylhydroxylamine derived from hydrogenated tallow amine.

7. Thiosynergists, for example dilauryl thiodipropionate, dimistryl thiodipropionate, distearyl thiodipropionate, pentaerythritol tetrakis[3-(dodecylthio)propionate] or distearyl disulfide.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilizers, for example copper salts in combination with iodides and/or phosphorus compounds and salts of divalent manganese.

10. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or zinc pyrocatecholate.

11. PVC heat stabilizer, for example, mixed metal stabilizers (such as Barium/Zinc, Calcium/Zinc type), Organotin stabilizers (such as organo tin mercaptester, -carboxylate, -sulfide), Lead stabilizers (such as Tribasic lead sulfate, Dibasic lead stearate, Dibasic lead phthalate, Dibasic lead phosphate, lead stearate), organic based stabilizers and combinations thereof.

12. Nucleating agents, for example inorganic substances, such as talcum, metal oxides, such as titanium dioxide or magnesium oxide, phosphates, carbonates or sulfates of, preferably, alkaline earth metals; organic compounds, such as mono- or polycarboxylic acids and the salts thereof, e.g. 4-tert-butylbenzoic acid, adipic acid, diphenylacetic acid, sodium succinate or sodium benzoate; polymeric compounds, such as ionic copolymers (ionomers). Especially preferred are 1,3:2,4-bis(3',4'-dimethylbenzylidene)sorbitol, 1,3:2,4-di(paramethyldibenzylidene)sorbitol, and 1,3:2,4-di (benzylidene)sorbitol.

13. Fillers and reinforcing agents, for example calcium carbonate, silicates, glass fibres, glass beads, asbestos, talc, kaolin, mica, barium sulfate, metal oxides and hydroxides, carbon black, graphite, wood flour and flours or fibers of other natural products, synthetic fibers.

14. Plasticizer, wherein said plasticizer is selected from the group consisting of Di(2-ethylhexyl) phthalate, Disononyl phthalate, Diisodecyl phthalate, Dipropylheptyl phthalate, Trioctyl trimellitate, Tri(isononyl) trimellitate, epoxidized soy bean oil, Di(isononyl) cyclohexane-1,2-dicarboxylate, 2,4,4-Trimethyl-1,3-pentaediol diisobutyrate.

The plasticizer as used in accordance with the invention may also comprise one selected from the group consisting of: phthalates, trimellitates, aliphatic dibasic esters, polyesters, polymeric, epoxides, phosphates. In a preferred embodiment said plasticizer is selected from the group consisting of: Butyl benzyl phthalate, Butyl 2-ethylhexyl phthalate, Diisohexyl phthalate, Diisoheptyl phthalate, Di(2-ethylhexyl) phthalate, Diisooctyl phthalate, Di-n-octyl phthalate, Disononyl phthalate, Diisodecyl phthalate, Diiso undecyl phthalate, Diisotredecyl phthalate, Diiso (C11, C12, C13) phthalate, Di(n-butyl) phthalate, Di(n-C7, C9) phthalate, Di(n-C6, C8, C10) phthalate, Diiso(n-nonyl) phthalate, Di(n-C7, C9, C11) phthalate, Di(n-C9, C11) phthalate, Di(n-undecyl) phthalate, Tri(n-C8, C10) trimellitate, Tri(2-ethylhexyl) trimellitate, Tri(isooctyl) trimellitate, Tri(isononyl) trimellitate, Di(n-C7, C9) adipate, Di(2-ethylhexyl) adipate, Di(isooctyl) adipate, Di(isononyl) adipate, Polyesters of adipinic acid or glutaric acid and propylene glycol or butylene glycol or 2,2-dimethyl-1,3-propanediol, Epoxidized oils such as epoxidized soy bean oil, epoxidized linseed oil, epoxidized tall oil, Octyl epoxy tallate, 2-ethylhexyl epoxy tallate, Isodecyl diphenyl phosphate, Tri(2-ethylhexyl) phosphate, Tricresyl phosphate, Di(2-ethylhexyl) terephthalate, Di(isononyl) cyclohexane-1,2-dicarboxylate and combinations thereof. In a particularly preferred embodiment said plasticizer is selected from the group consisting of: Diisohexyl phthalate, Diisoheptyl phthalate, Di(2-ethylhexyl) phthalate, Diisooctyl phthalate, Di-n-octyl phthalate, Disononyl phthalate, Diisodecyl phthalate, Diiso undecyl phthalate, Diisotredecyl phthalate, Diiso (C11, C12, C13) phthalate, Di(n-butyl) phthalate, Di(n-C7, C9) phthalate, Di(n-C6, C8, C10) phthalate, Diiso (n-nonyl) phthalate, Di(n-C7, C9, C11) phthalate, Di(n-C9, C11) phthalate, Di(n-undecyl) phthalate, Tri(n-C8, C10) trimellitate, Tri(2-ethylhexyl) trimellitate, Tri(isooctyl) trimellitate, Tri(isononyl) trimellitate, Di(n-C7, C9) adipate, Di(2-ethylhexyl) adipate, Di(isooctyl) adipate, Di(isononyl) adipate, Polyesters of adipinic acid or glutaric acid and propylene glycol or butylene glycol or 2,2-dimethyl-1,3-propanediol, Epoxidized oils such as epoxidized soy bean oil, Di(isononyl) cyclohexane-1,2-dicarboxylate and combinations thereof.

15. Other additives, for example plasticisers, lubricants, emulsifiers, pigments, rheology additives, catalysts, flow-control agents, optical brighteners, flameproofing agents, antistatic agents and blowing agents.

16. Benzofuranones and indolinones, for example those disclosed in U.S. Pat. Nos. 4,325,863; 4,338,244; 5,175,312; 5,216,052; 5,252,643; DE-A-4316611; DE-A-4316622; DE-A-4316876; EP-A-0589839, EP-A-0591102; EP-A-1291384 or 3-[4-(2-acetoxyethoxy)phenyl]-5,7-di-tert-butylbenzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzofuran-2-one, 3-(3,4-dimethylphenyl)-5,7-di-tert-butylbenzofuran-2-one, 3-(2,3-dimethylphenyl)-5,7-di-tert-butylbenzofuran-2-one, 3-(2-acetyl-5-isooctylphenyl)-5-isooctylbenzofuran-2-one.

Compounding ingredients such as pigments, colouring agents, fillers, extenders, flame retardants, antiozonants, antioxidants, mould release agents, acid scavengers, plasticizers, stabilisers such as pH stabilisers, emulsifiers, vulcanising agents, polymerisation initiators, sensitisers and the like may be incorporated into the polymeric composition.

A further embodiment of the present invention is a shaped article made of the polymeric composition of the present invention:

Examples of suitable shaped articles are:

I-1) Floating devices, marine applications, pontoons, buoys, plastic lumber for decks, piers, boats, kayaks, oars, and beach reinforcements.

I-2) Automotive applications, interior applications, exterior applications, in particular trims, bumpers, dashboards, battery, rear and front linings, moldings parts under the hood, hat shelf, trunk linings, interior linings, air bag covers, electronic moldings for fittings (lights), panes for dashboards, headlamp glass, instrument panel, exterior linings, upholstery, automotive lights, head lights, parking lights, rear lights, stop lights, interior and exterior trims; door panels; gas tank; glazing front side; rear windows; seat backing, exterior panels, wire insulation, profile extrusion for sealing, cladding, pillar covers, chassis parts, exhaust systems, fuel filter/filler, fuel pumps, fuel tank, body side mouldings, convertible tops, exterior mirrors, exterior trim, fasteners/fixings, front end module, glass, hinges, lock systems, luggage/roof racks, pressed/stamped parts, seals, side impact protection, sound deadener/insulator and sunroof, door medallion, consoles, instrument panels, seats, frames, skins, automotive applications reinforced, automotive applications fiber reinforced, automotive applications with filled polymers, automotive applications with unfilled polymers.

I-3) Road traffic devices, in particular sign postings, posts for road marking, car accessories, warning triangles, medical cases, helmets, tires.

I-4) Devices for transportation or public transportation. Devices for plane, railway, motor car (car, motorbike), trucks, light trucks, busses, trams, bikes including furnishings.

I-5) Devices for space applications, in particular rockets and satellites, e.g. reentry shields.

I-6) Devices for architecture and design, mining applications, acoustic quietized systems, street refuges, and shelters.

II-1) Appliances, cases and coverings in general and electric/electronic devices (personal computer, telephone, portable phone, printer, television-sets, audio and video devices), flower pots, satellite TV bowl, and panel devices.

II-2) Jacketing for other materials such as steel or textiles.

II-3) Devices for the electronic industry, in particular insulation for plugs, especially computer plugs, cases for electric and electronic parts, printed boards, and materials for electronic data storage such as chips, check cards or credit cards.

II-4) Electric appliances, in particular washing machines, tumblers, ovens (microwave oven), dish-washers, mixers, and irons.

II-5) Covers for lights (e.g. street-lights, lamp-shades).

II-6) Applications in wire and cable (semi-conductor, insulation and cable-jacketing).

II-7) Foils for condensers, refrigerators, heating devices, air conditioners, encapsulating of electronics, semi-conductors, coffee machines, and vacuum cleaners.

III-1) Technical articles such as cogwheel (gear), slide fittings, spacers, screws, bolts, handles, and knobs.

III-2) Rotor blades, ventilators and windmill vanes, solar devices, closets, wardrobes, dividing walls, slat walls, folding walls, roofs, shutters (e.g. roller shutters), fittings, connections between pipes, sleeves, and conveyor belts.

III-3) Sanitary articles, in particular mobile toilets, shower cubicles, lavatory seats, covers, and sinks.

III-4) Hygienic articles, in particular diapers (babies, adult incontinence), feminine hygiene articles, shower curtains, brushes, mats, tubs, mobile toilets, tooth brushes, and bed pans.

III-5) Pipes (cross-linked or not) for water, waste water and chemicals, pipes for wire and cable protection, pipes for gas, oil and sewage, guttering, down pipes, and drainage systems.

III-6) Profiles of any geometry (window panes), cladding and siding.

III-7) Glass substitutes, in particular extruded plates, glazing for buildings (monolithic, twin or multiwall), aircraft, schools, extruded sheets, window film for architectural glazing, train, transportation and sanitary articles.

III-8) Plates (walls, cutting board), silos, wood substitute, plastic lumber, wood composites, walls, surfaces, furniture, decorative foil, floor coverings (interior and exterior applications), flooring, duck boards, and tiles.

III-9) Intake and outlet manifolds.

III-10) Cement-, concrete-, composite-applications and covers, siding and cladding, hand rails, banisters, kitchen work tops, roofing, roofing sheets, tiles, and tarpaulins.

IV-1) Plates (walls and cutting board), trays, artificial grass, astroturf, artificial covering for stadium rings (athletics), artificial floor for stadium rings (athletics), and tapes.

IV-2) Woven fabrics continuous and staple, fibers (carpets/hygienic articles/geotextiles/monofilaments; filters; wipes/curtains (shades)/medical applications), bulk fibers (applications such as gown/protection clothes), nets, ropes, cables, strings, cords, threads, safety seatbelts, clothes, underwear, gloves; boots; rubber boots, intimate apparel, garments, swimwear, sportswear, umbrellas (parasol, sunshade), parachutes, paraglides, sails, "balloon-silk", camping articles, tents, airbeds, sun beds, bulk bags, and bags.

IV-3) Membranes, insulation, covers and seals for roofs, geomembranes, tunnels, dumps, ponds, walls roofing membranes, geomembranes, swimming pools, swimming pool liners, pool liners, pond liners, curtains (shades)/sun-shields, awnings, canopies, wallpaper, food packing and wrapping (flexible and solid), medical packaging (flexible & solid), airbags/safety belts, arm- and head rests, carpets, centre console, dashboard, cockpits, door, overhead console module, door trim, headliners, interior lighting, interior mirrors, parcel shelf, rear luggage cover, seats, steering column, steering wheel, textiles, and trunk trim.

V-1) Films (packaging, rigid packaging, dump, laminating, bale wrap, swimming pools, waste bags, wallpaper, stretch film, raffia, desalination film, batteries, and connectors.

V-2) Agricultural films (greenhouse covers, tunnel, multi-tunnel, micro-tunnel, "raspa y amagado", multi-span, low walk-in tunnel, high tunnel, mulch, silage, silo-bags, silo-stretch, fumigation, air bubble, keder, solawrap, thermal, bale wrap, stretched bale wraps, nursery, film tubes), especially in presence of intensive application of agrochemicals; other agricultural applications (e.g. non-woven soil covers, nets (made of tapes, multi-filaments and combinations thereof), tarpaulins. Such an agricultural film can either be a mono-layer structure or a multi-layer structure, typically made of three, five or seven layers. This can lead to a film structure like A-B-A, A-B-C, A-B-C-B-A, A-B-C-B-D, A-B-C-D-C-B-A, A-A-B-C-B-A-A. A, B, C, D represent the different polymers and tackifiers. However adjacent layers can also be coupled so that the final film article can be made of an even number of layers, i.e. two, four or six layers such as A-A-B-A, A-A-B-B, A-A-B-A-A, A-B-B-A-A, A-A-B-C-B, A-A-B-C-A-A and the like.

V-3) Tapes

V-4) Foams (sealing, insulation, barrier), sport and leisure mats.

V-5) Sealants

VI-1) Food packing and wrapping (flexible and solid), BOPP, BOPET, bottles.

VI-2) Storage systems such as boxes (crates), luggage, chest, household boxes, pal-lets, container, shelves, tracks, screw boxes, packs, and cans.

VI-3) Cartridges, syringes, medical applications, containers for any transportation, waste baskets and waste bins, waste bags, bins, dust bins, bin liners, wheely bins, container in general, tanks for water/used water/chemistry/gas/oil/gasoline/diesel; tank liners, boxes, crates, battery cases, troughs, medical devices such as piston, ophthalmic applications, diagnostic devices, and packing for pharmaceuticals blister.

VII-1) Household articles of any kind (e.g. appliances, thermos bottle/clothes hanger), fastening systems such as plugs, wire and cable clamps, zippers, closures, locks, and snap-closures.

VII-2) Support devices, articles for the leisure time such as sports and fitness devices, gymnastics mats, ski-boots, inline-skates, skis, big foot, athletic surfaces (e.g. tennis grounds); screw tops, tops and stoppers for bottles, and cans.

VII-3) Furniture in general, foamed articles (cushions, impact absorbers), foams, sponges, dish clothes, mats, garden chairs, stadium seats, tables, couches, toys, building kits (boards/figures/balls), playhouses, slides, and play vehicles.

VII-4) Materials for optical and magnetic data storage.

VII-5) Kitchen ware (eating, drinking, cooking, storing).

VII-6) Boxes for CD's, cassettes and video tapes; DVD electronic articles, office sup-plies of any kind (ball-point pens, stamps and ink-pads, mouse, shelves, tracks), bottles of any volume and content (drinks, detergents, cosmetics including perfumes), and adhesive tapes.

VII-7) Footwear (shoes/shoe-soles), insoles, spats, adhesives, structural adhesives, food boxes (fruit, vegetables, meat, fish), synthetic paper, labels for bottles, couches, artificial joints (human), printing plates (flexographic), printed circuit boards, and display technologies.

VII-8) Devices of filled polymers (talc, chalk, china clay (kaolin), wollastonite, pigments, carbon black, TiO2, mica, nanocomposites, dolomite, silicates, glass, asbestos).

It has been found by the applicant that zinc monoglycerolate containing crystallite size described herein, and/or prepared according to the process described herein, provides improved crystallization characteristics. These improvements are particularly evident for propylene homo-polymer and copolymers and polypropylene blends. These improvements include the following:

1. Higher Tc results at lower nucleating agent loadings. At 200 ppm addition to isotactic polypropylene (hereafter "iPP"-LyondellBasell, Moplen HP400N isotactic polypropylene homopolymer, MFI=11 g/10 min), glycerol monostearate-modified zinc monoglycerolate (GMS-ZMG) gives a Tc of 124.1° C., whereas unmodified ZMG affords a Tc of only 120.6° C. To obtain a Tc of 123.8° C. (approximately same as with GMS-ZMG at 200 ppm), 600 ppm ZMG is required. The Tc for HP400N (without nucleating agent) is 117.0° C. 2. The time taken to achieve 50% polymer crystallisation ($t_{1/2}$) at 140° C. are considerably improved (shortened) at 200 ppm using the modified ZMG of the present application compared to unmodified ZMG: GMS-ZMG gives a $t_{1/2}$ of 7.2 min vs the $t_{1/2}$ for ZMG of 14.6 min. To achieve a $t_{1/2}$ of 7.1 min using unmodified ZMG alone, 600 ppm of ZMG is required instead. HP400N, by itself, does not crystallise within 40 min.

The modified zinc monoglycerolate (GMS-ZMG) provides an increase in the Tc of approximately 3.4° C. at 200 ppm in isotactic polypropylene, as compared to the same loading of unmodified zinc monoglycerolate.

In compositions based on polyolefins as the organic polymer, the use of zinc monoglycerolate at a given loading level in the polyolefin provides a higher crystallisation temperature for the polyolefin than is achieved with the same loading level of a zinc monoglycerolate having a crystallite size of greater than 30 nm in the <100> direction, or of greater than 60 nm in the <011> direction, or having an aspect ratio computed by <100>/<011> coherent domain lengths that is greater than 0.65 (i.e. when compared to a zinc monoglycerolate that is unmodified zinc monoglycerolate, or the Bos-form of zinc monoglycerolate). In isotactic polypropylene, the use of the modified zinc monoglycerolate of the present application at a given loading level in the isotactic polypropylene provides a time to achieve 50% polymer crystallisation ($t_{1⁄2}$) at 140° C. that is at least 40% less than that achieved with the same loading of the comparison zinc monoglycerolate (i.e. one having a crystallite size of greater than 30 nm in the <100> direction, or of greater than 60 nm in the <011> direction, or having an aspect ratio computed by <100>/<011> coherent domain lengths that is greater than 0.65).

In the claims and in the preceding description, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

EXAMPLES

The invention will now be described in further detail with reference to the following non-limiting examples.
Procedures
Characterisation Techniques XRD analysis was performed using the Phillips 1140 Diffractometer, employing a copper source (40 kV, 25 mA) and graphite monochromators or Bruker D2 Phaser employing a copper source (30 kV, 10 mA), set up according to the Bragg-Brentano (θ-2θ) geometry. Scanning was between the desired 2θ values (2θ=5-35°). E.g. "Powder samples were mounted on a standard sample holder (mg-few g). Polymer samples were extruded in an extruder, and pressed between metal plates to obtain a flat piece, cooled in a water bath, and cut to size, so as to fit in the sample holder available (<3 mm thickness).

The mean crystallite size (average coherence domain length) in each of the <100> and (011) directions was calculated using the Scherrer equation, using the measured full width at half maximum (FWHM) value measured by XRD (β), the X-ray wavelength (λ), Bragg angle (expressed in degrees; (2θ value of peak)/2)), the dimensionless shape factor (K, taken to be 0.9; same K was used always, for comparison). The Scherrer equation is $τ=Kλ/β \cos θ$. Note that line broadening owing to the instrument is ignored, and line broadening is assumed to be from coherent domain length changes alone.

SEM microscopy was performed using a JEOL JSM-7001F Scanning Electron Microscope. Samples were mounted on a carbon tape and sputter coated with Pt.

The samples for the crystallisation tests were prepared as follows: Semi-crystalline isotactic polypropylene (iPP) homopolymer bare resin (Moplen HP400N (from Lyondell-Basell, Australia) was used as the iPP. Samples of iPP containing no nucleating agent (control), or a specified amount of a nucleating agent were prepared by mixing iPP with the required amount of nucleating agent. Thorough manual mixing was carried out first (powder+iPP beads) followed by extrusion. 1 wt % or 2000 ppm masterbatches (depending upon the set of comparative experiments) were prepared and extruded. Extruded strands were pelletized and extruded again at the desired concentration (200 or 600 ppm). (In one case, noted explicitly, the 200 ppm material has been extruded twice). The extruder employed was a CRD barrier, single-screw (dia.=25 mm; L/D=25) extruder, manufactured by Rauwendaal Extrusion Eng. Inc. attached to a Haake Rheocord 90. The four temperature zones were set to be 170, 175, 180 and 180° C. (die) respectively. The screw speed was 100 rpm.

Example 1—Preparation of GMS Modified Zinc Monoglycerolate (GMS-ZMG)

ZnO (656.4 g) and GMS (72.3 g) were homogenised and heated in a Z-blade mixer. Then 668.5 g of glycerol was added. Then 74.3 g glycerol+8.7 g water+4.5 g 90% acetic acid was added, and further homogenised. The temperature was raised to 110° C. Once fully reacted, i.e. fine dry powder, the heat was switched off. The highest temperature reached was around 120° C., but the temperature during the reaction was largely within the 100-120° C. range. Mixing within this temperature range continued after the reaction was complete, during which time the agglomerated product formed. The resulting agglomerated (powder) product was pin milled.

Figure 2A:
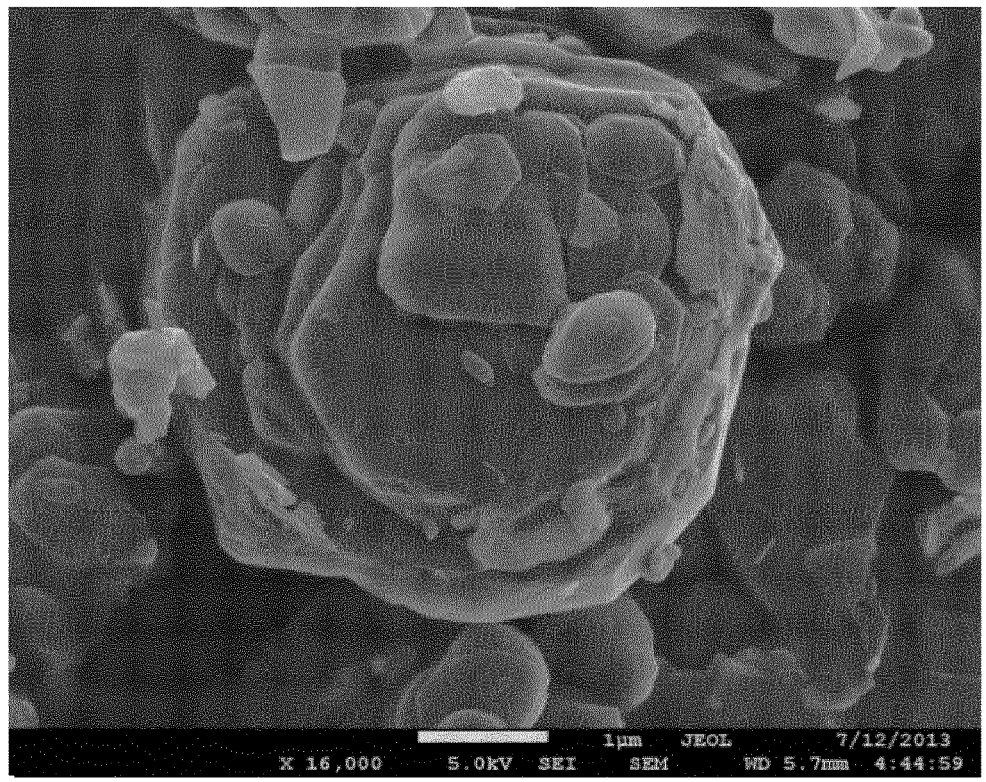
FIGS. 2a and 2b show the SEM images of unmodified ZMG (FIG. 2a) and modified ZMG (FIG. 2b) of an embodiment of the invention. The scale bar in each image is 1 µm.
Figure 2B:
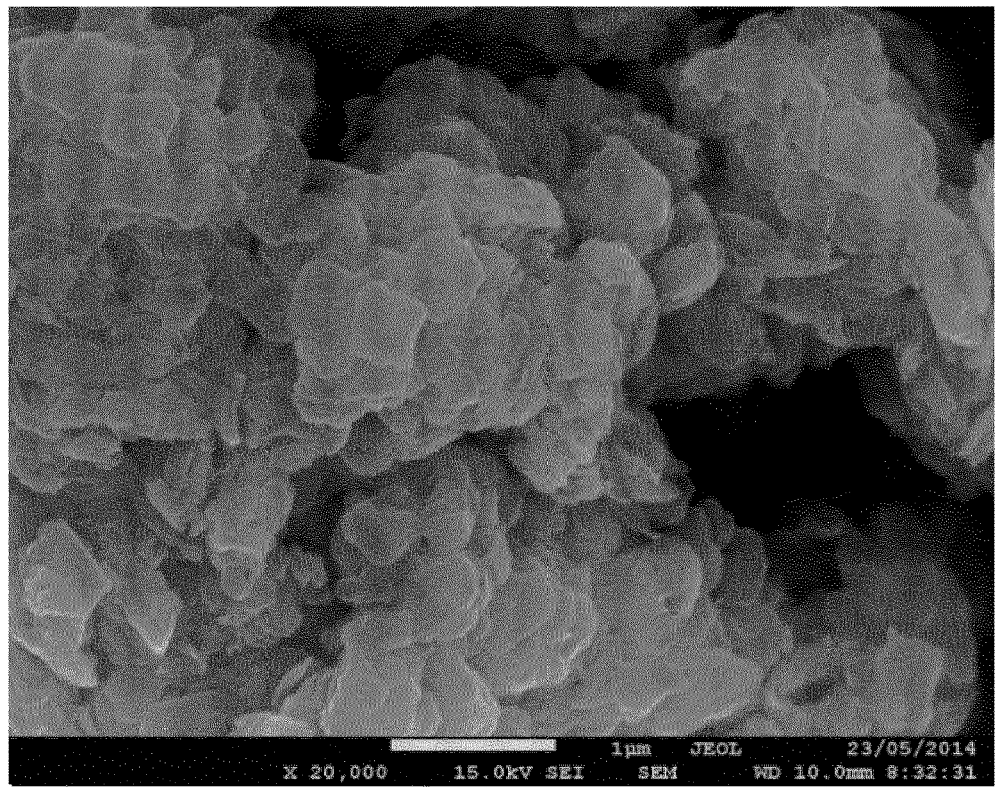

XRD analysis was then performed to determine the mean crystallite size. The XRD pattern is set out in FIG. 1. One of the lines in the XRD pattern of FIG. 1 is for the product of Example 1 (marked GMS-ZMG), and the second is for an unmodified ZMG. The peak at 2θ=10.9° is owing to the set of planes described by the (100) miller index (stack of cards). The coherence domain length (crystallite size) in the <100> direction for the GMS-ZMG of Example 1 was calculated to be 17 nm, compared to 40 nm for a sample of unmodified ZMG. The peak at 2θ=17.2° corresponds to the set of planes described by the miller index (011) (planes within each card). The crystallite size in this direction is 45 nm for both GMS-ZMG and unmodified ZMG. SEM imaging was performed on the agglomerated product of Example 1, compared to that of the unmodified ZMG. The SEM images are shown in FIGS. 2a and 2b. The scale bar in each image is 1 μm. The two products have different morphologies. The image of FIG. 2a (A) is of the unmodified ZMG. The image of FIG. 2b (B) is of the GMS-ZMG product of Example 1. The product of Example 1 shows agglomerated collections of crystallites. The agglomerated crystallites show a "fishscale"-like surface pattern (on individual particles), indicating that much smaller crystallites stack imperfectly, with the edges exposed.

Figure 3A:
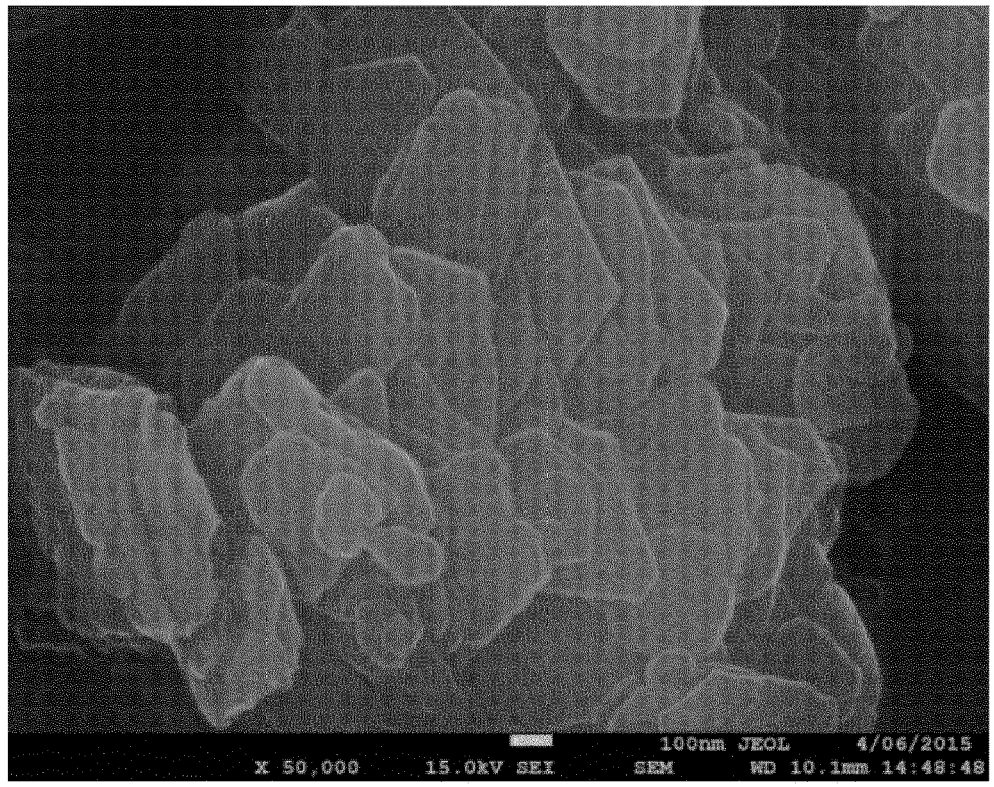
FIGS. 3a, 3b and 4 are additional SEM images for the modified zinc monoglycerolate. The scale bar in each image is 100 nm.
Figure 3B:
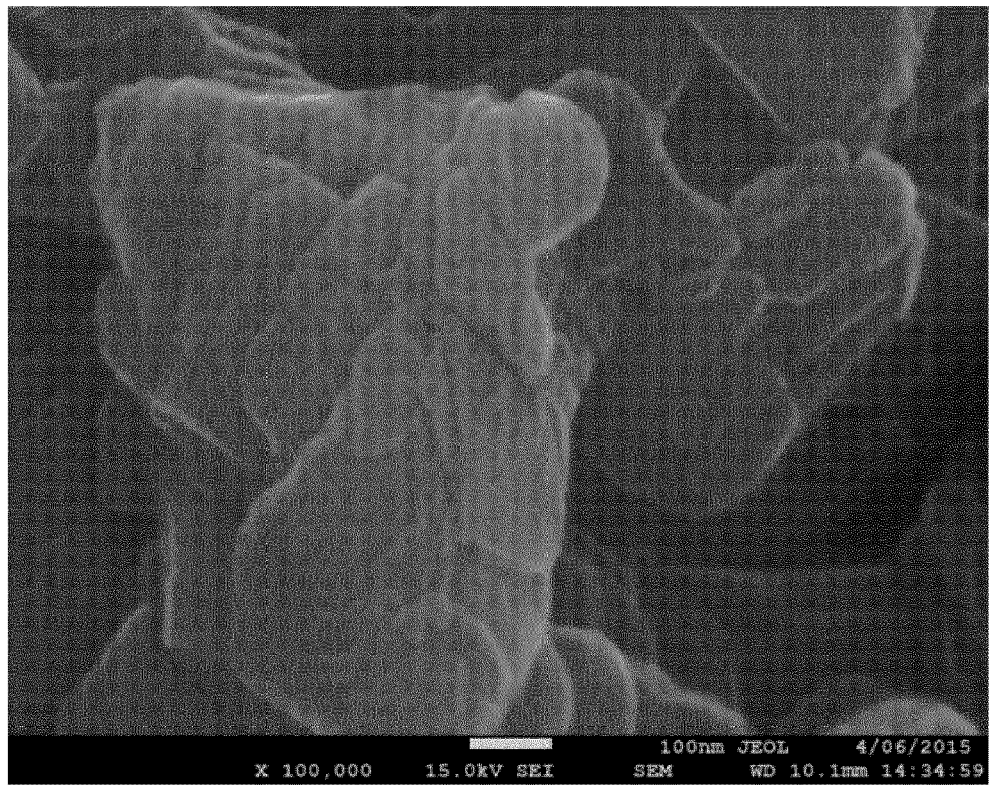
Figure 4:
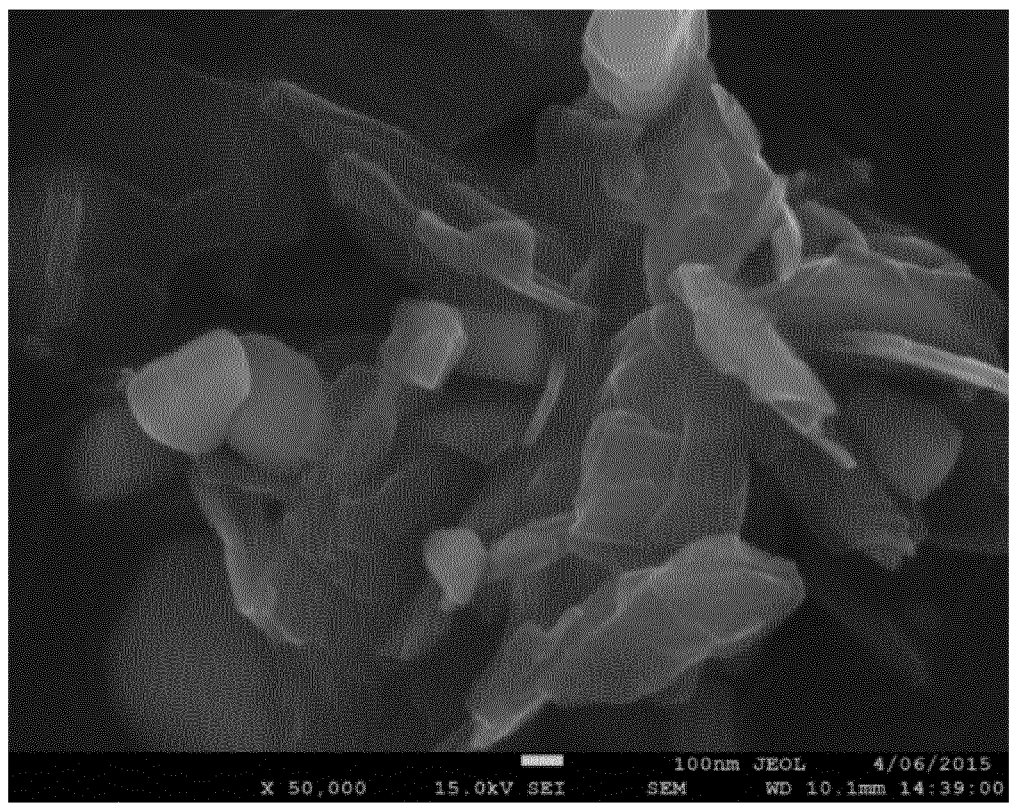

Additional SEM images of the GMS-ZMG product of Example 1 are shown in FIGS. 3a, 3b and 4.

Samples of iPP (isotactic polypropylene) were prepared containing 200 ppm of the unmodified ZMG, 600 ppm of the unmodified ZMG, 200 ppm of the GMS-ZMG of Example 1, and a control with no nucleating agent ("blank"). The crystallization behavior of the samples was assessed, using Differential Scanning calorimetry (DSC), whereby heat flow (in/out of the sample) (in mW) was measured against sample temperature (degrees C.), to assess the crystallization temperature for the polypropylene sample containing the nucleating agent.

The following table shows the results in tabular form:

| Sample | Tc |
|---|---|
| 600 ppm unmodified ZMG | 123.8° C. |
| 200 ppm unmodified ZMG | 120.6° C. |
| 200 ppm GMS-ZMG | 124.1° C. |
| iPP only (HP400N) | 117.0° C. |

The above Table shows that the Tc for the sample containing 200 ppm of the GMS-ZMG of Example 1 is about the same as that for the sample containing 600 ppm (three times the amount) of unmodified ZMG. The Tc is higher with 200 ppm of the GMS-ZMG of Example 1, compared to the same amount of unmodified ZMG.

A similar trend can be seen for isothermal $t_{1/2}$ at 140° C.:

| Sample | $t_{1/2}$ |
|---|---|
| 600 ppm unmodified ZMG | 7.1 min |
| 200 ppm unmodified ZMG | 14.6 min |
| 200 ppm GMS-ZMG | 7.2 min |
| iPP only (HP400N) | Does not crystallise within 40 minutes. |

Comparative Example

Wet hydrozincite (equivalent to 50.0 kg zinc oxide) was slowly added to glycerol (53.5 kg) with mixing, in a sigma mixer. Glycerol monostearate (5.0 kg) was slowly added with mixing, and the composition mixed to a thin paste. The mixture contained significant water from the hydrozincite—the amount was calculated to be 70% by weight of water in the slurry of hydrozincite-water employed, or 1410 mol % with respect to the zinc in the reaction composition. The composition was heated to 160° C. and held at this temperature for 16 hours. A dry flowable powder was produced.

The above description is effectively that of Bos 2006. The product so produced is referred to as "hydrozincite-ZMG".

Figure 5:
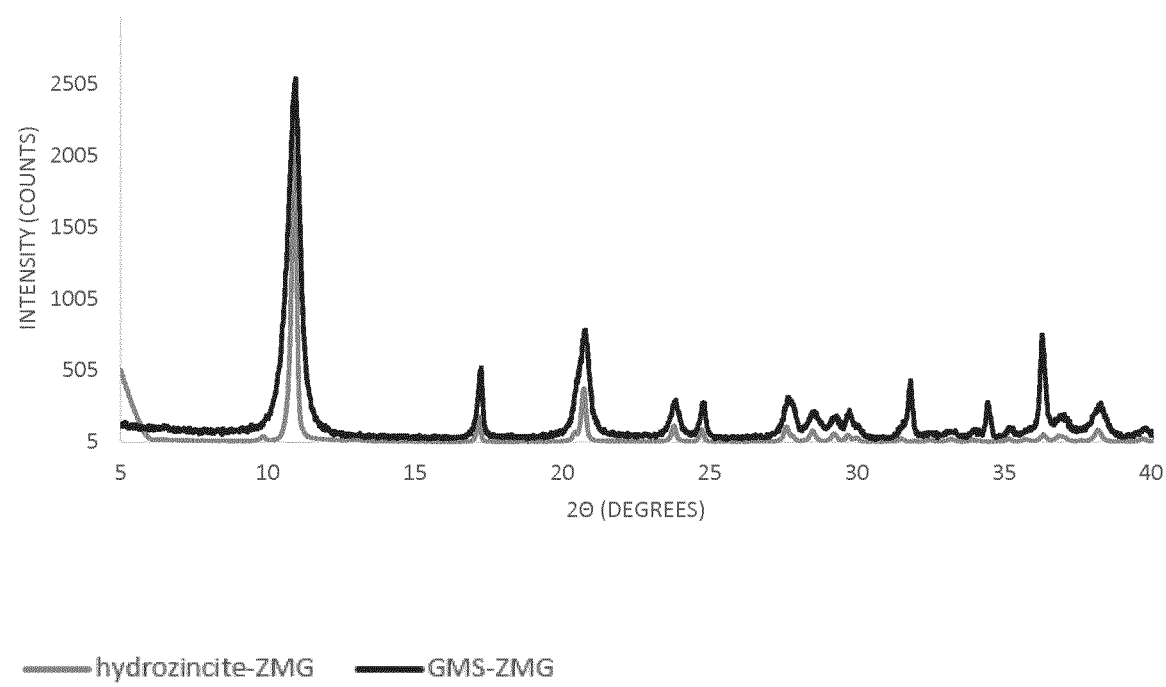
FIG. 5 shows the XRD pattern of hydrozincite-ZMG (comparative example 1), compared with XRD plot of GMS-ZMG (Example 1). The X-axis is the 2θ axis (in degrees), and the Y-axis is the count. The line at 2θ=10.9° is the (100) peak, and the two XRD patterns have been normalized such that (100) peak intensities are the same. The (100) peak of GMS-ZMG is broader than in hydrozincite-ZMG, i.e. GMS-ZMG crystallites are smaller.

The crystallite size of the powder produced (hydrozincite-ZMG) was measured using XRD (FIG. 5), and the results are presented in the table below, together with the crystallite size measurements for the product of Example 1 (GMS-ZMG), and unmodified ZMG. Also included in the table are the computed <100>/<011> aspect ratio values:

| Example | <100> size | <011> size | <100>/<011> aspect ratio |
|---|---|---|---|
| hydrozincite-ZMG of comparative example | 44 nm | 57 nm | 0.77 |
| Unmodified ZMG | 40 nm | 45 nm | 0.89 |
| GMS-ZMG of Example 1 | 17 nm | 45 nm | 0.38 |

The crystallite size in the <100> direction for hydrozincite-ZMG (Comparative Example) is roughly similar to that of unmodified ZMG, but it is significantly higher than that for the GMS-ZMG Example 1. Notably, the crystallite size in the <011> direction is of the same order of magnitude as that of GMS-ZMG, in all three cases (although hydrozincite-ZMG is slightly longer). In the GMS-ZMG (Example 1), although the <011> crystallite size remains largely similar (size of layers), the <100> crystallite size (thickness of stacks of layers) shrinks considerably. The <100>/<011> aspect ratio of GMS-ZMG is usually less than 0.65, and is often less than 0.44; in this case 0.38). Clearly, this is smaller than in both unmodified ZMG and GMS-ZMG. In other words, the GMS modification of ZMG according to the current invention creates smaller stacks of ZMG layers (which can disperse more efficiently in the polymer), as compared to the other two types (unmodified ZMG and hydrozincite-ZMG).

Example A

Samples of iPP (isotactic polypropylene, homopolymer, melt flow index 8 dg/min at 230° C./2.16 kg) were prepared containing 100 ppm, 200 ppm, 600 ppm or 1200 ppm of the unmodified ZMG or of the GMS-ZMG, and a control with no nucleating agent ("blank").

The crystallite size of the unmodified ZMG and of the GMS-ZMG was measured using XRD and the results are presented in the table below. Also included are the computed <100>/<011> aspect ratio values:

| Example | <100> size | <011> size | <100>/<011> aspect ratio |
|---|---|---|---|
| Unmodified ZMG | 40 nm | 45 nm | 0.89 |
| GMS-ZMG | 25 nm | 47 nm | 0.53 |

The crystallization behavior of the samples was assessed, using Differential Scanning calorimetry (DSC), whereby heat flow (in/out of the sample) (in mW) was measured against sample temperature (degrees C.), to assess the crystallization temperature for the polypropylene sample containing the nucleating agent.

The following table shows the results in tabular form:

| Sample | Tc |
|---|---|
| 1200 ppm unmodified ZMG | 123.7° C. |
| 600 ppm unmodified ZMG | 126.7° C. |
| 200 ppm unmodified ZMG | 124.4° C. |
| 100 ppm unmodified ZMG | 122.1° C. |
| 1200 ppm GMS-ZMG | 130.6° C. |
| 600 ppm GMS-ZMG | 129.2° C. |
| 200 ppm GMS-ZMG | 127.2° C. |
| 100 ppm GMS-ZMG | 125.8° C. |
| iPP only (HD120 MO) | 114.9° C. |

The above Table shows that the Tc for the sample containing 100 ppm of the GMS-ZMG is about the same as that for the sample containing 600 ppm (six times the amount) of unmodified ZMG. At any concentration over this extended range of concentrations, the Tc of the GMS-ZMG is higher, compared to the Tc with the same amount of unmodified ZMG.

Among the samples prepared with these compounds, plates (2 mm thick) were injected. Dumbbells with shape according to ISO 527-2 5A (year 2012) were die-cut in the sense of the melt flow and the tensile properties were tested according to ISO 527 (year 2012). The results (E-modulus and strength at yield) are presented in the below table. The same trend as for the crystallization temperature is observed.

| Sample | E-modulus (*) | Yield strength (*) |
|---|---|---|
| 1200 ppm unmodified ZMG | 1838 MPa | 41.98 MPa |
| 600 ppm unmodified ZMG | 1759 MPa | 40.97 MPa |
| 200 ppm unmodified ZMG | 1707 MPa | 40.33 MPa |

| Sample | E-modulus (*) | Yield strength (*) |
| --- | --- | --- |
| 100 ppm unmodified ZMG | 1676 MPa | 40.01 MPa |
| 1200 ppm GMS-ZMG | 1857 MPa | 41.99 MPa |
| 600 ppm GMS-ZMG | 1842 MPa | 41.68 MPa |
| 200 ppm GMS-ZMG | 1794 MPa | 41.33 MPa |
| 100 ppm GMS-ZMG | 1730 MPa | 40.65 MPa |
| iPP only (HD120 MO) | 1648 MPa | 39.99 MPa |

(*) High values are desired

The above Table shows that the E-modulus and the yield strength for the sample containing 200 ppm of the GMS-ZMG are significantly higher than that for the sample containing 600 ppm (three times the amount) of unmodified ZMG. At any concentration over this wide range of concentrations, the E-modulus and the yield strength of the GMS-ZMG are higher, compared to the E-modulus resp. yield strength with the same amount of unmodified ZMG.

Example B

Samples of iPP (isotactic polypropylene, homopolymer, melt flow index 19 dg/min at 230° C./2.16 kg) were prepared containing 200 ppm of the unmodified ZMG, 600 ppm of the unmodified ZMG, 200 ppm of the GMS-ZMG of the above example or 600 ppm of the GMS-ZMG of the above example, and a control with no nucleating agent ("blank"). The crystallization behavior of the samples was assessed, using Differential Scanning calorimetry (DSC), whereby heat flow (in/out of the sample) (mW) was measured against sample temperature (degrees C.), to assess the crystallization temperature for the polypropylene sample containing the nucleating agent. The following table shows the results in tabular form:

| Sample | Tc |
| --- | --- |
| 600 ppm unmodified ZMG | 126.0° C. |
| 200 ppm unmodified ZMG | 123.5° C. |
| 600 ppm GMS-ZMG | 128.3° C. |
| 200 ppm GMS-ZMG | 125.8° C. |
| iPP only (HF420 FB) | 116.2° C. |

The above Table shows that the Tc for the sample containing 200 ppm of the GMS-ZMG is about the same as that for the sample containing 600 ppm (three times the amount) of unmodified ZMG. The Tc is higher with all concentrations of the GMS-ZMG, compared to the same amount of unmodified ZMG.

Among the samples prepared with these compounds, plates (2 mm thick) were injected. Dumbbells with shape according to ISO 527-2 5A (year 2012) were die-cut in the sense of the melt flow and the tensile properties were tested according to ISO 527 (year 2012). The results (E-modulus and strength at yield) are presented in the below table. The same trend as for the crystallization temperature is observed.

| Sample | E-modulus (*) | Yield strength (*) |
| --- | --- | --- |
| 600 ppm unmodified ZMG | 1511 MPa | 37.98 MPa |
| 200 ppm unmodified ZMG | 1457 MPa | 37.11 MPa |
| 600 ppm GMS-ZMG | 1604 MPa | 38.78 MPa |
| 200 ppm GMS-ZMG | 1534 MPa | 38.19 MPa |
| iPP only (HF420 FB) | 1362 MPa | 35.37 MPa |

(*) High values are desired

The above Table shows that the E-modulus and the yield strength for the sample containing 200 ppm of the GMS-ZMG are significantly higher than that for the sample containing 600 ppm (three times the amount) of unmodified ZMG. At any concentration over this range of concentrations, the E-modulus and the yield strength of the GMS-ZMG are higher, compared to the E-modulus resp. yield strength with the same amount of unmodified ZMG.

Example C

Samples of iPP raco (isotactic polypropylene, random copolymer, melt flow index 8 dg/min at 230° C./2.16 kg) were prepared containing 200 ppm of the unmodified ZMG or 200 ppm of the GMS-ZMG of the above example and a control with no nucleating agent ("blank"). The crystallization behavior of the samples was assessed, using Differential Scanning calorimetry (DSC), whereby heat flow (in/out of the sample) (in mW) was measured against sample temperature (degrees C.), to assess the crystallization temperature for the polypropylene sample containing the nucleating agent.

The following table shows the results in tabular form:

| Sample | Tc |
| --- | --- |
| 200 ppm unmodified ZMG | 116.2° C. |
| 200 ppm GMS-ZMG | 118.4° C. |
| iPP raco only (RD204 CF) | 114.2° C. |

The above Table shows that the Tc for the sample containing 200 ppm of the GMS-ZMG is significantly higher than the Tc of the unmodified ZMG at the same concentration.

Among the samples prepared with these compounds, plates (2 mm thick) were injected. Dumbbells with shape according to ISO 527-2 5A (year 2012) were die-cut in the sense of the melt flow and the tensile properties were tested according to ISO 527 (year 2012). The results (E-modulus and strength at yield) are presented in the below table. The same trend as for the crystallization temperature is observed.

| Sample | E-modulus (*) | Yield strength (*) |
| --- | --- | --- |
| 200 ppm unmodified ZMG | 1262 MPa | 34.39 MPa |
| 200 ppm GMS-ZMG | 1300 MPa | 34.43 MPa |
| iPP raco only (RD204 CF) | 1207 MPa | 33.70 MPa |

(*) High values are desired

The above Table shows that the E-modulus ad the yield strength for the sample containing 200 ppm of the GMS-ZMG are higher than that for the sample of unmodified ZMG at the same concentration.

The invention claimed is:
1. A zinc monoglycerolate in the firm of agglomerates of crystallites, wherein:
   a crystallite size of the zinc monoglycerolate, based on average coherence domain length, is less than 30 nm in the <100> direction, which is along the <100> zone axis, and less than 60 nm in the <011> direction, which is along the <100> zone axis, as determined by the Scherrer equation via powder X-ray diffraction;
   an aspect ratio of the zinc monoglycerolate, computed by <100>/<011> coherent domain lengths, is less than 0.65; and wherein the zinc monoglycerolate is obtained by a process comprising reacting glycerol with a zinc compound, which is different from hydrozincite and is not derived from hydrozincite.

2. The zinc monoglycerolate according to claim comprising a modifier.

3. The zinc monoglycerolate according to claim 2, wherein the modifier is a glycerol carboxylate ester.

4. The zinc monoglycerolate according to claim 3, wherein the glycerol carboxylate ester is a saturated fatty acid ester of glycerol.

5. The zinc monoglycerolate according to claim 4, wherein the glycerol carboxylate ester is glycerol monostearate.

6. The zinc monoglycerolate according to claim 2, wherein an amount of modifier is between 1.0 and 5.0 mol % with respect to the zinc monoglycerolate.

7. A zinc monoglycerolate in the form of agglomerates of crystallites, comprising between 1.0 and 5.0 mol % of a glycerol carboxylate ester.

8. A process for preparing the zinc monoglycerolate according to claim 1, the process comprising reacting all the zinc compound with glycerol and a modifier in the presence of an acid catalyst, wherein at least one of the following conditions is satisfied:
the zinc compound is selected from the group consisting of zinc oxide, zinc carbonate, zinc hydroxide, zinc carboxylate and combinations thereof, and
the reaction is conducted in the presence of less than 10% by weight water, based on the total weight of the reaction composition.

9. The process according to claim 8, wherein the modifier is a glycerol carboxylate ester.

10. The process according to claim 8, wherein an amount of the glycerol is between 90 and 110 mol % with respect to the zinc compound.

11. The process according to claim 8, wherein an amount of the modifier is between 1.0 and 5.0 mol % with respect to the zinc compound.

12. The process according to claim 8, wherein an amount of the acid catalyst is between 0.2 and 5 mol % with respect to the zinc compound.

13. A zinc monoglycerolate obtained by the process of claim 8.

14. A composition, comprising an organic polymer and the zinc monoglycerolate of claim 1.

15. The composition according to claim 14, wherein the organic polymer is selected from the group consisting of a polyolefin, a polyvinyl chloride, a polystyrene, a polyacrylamide, a polyester, a polyamide, copolymers thereof, and copolymers of one or more of acrylonitrile, butadiene and styrene with each other or with another co-monomers.

16. The composition according to claim 14, wherein the zinc monoglycerolate is present in an amount of 0.001% to 20% relative to the weight of the organic polymer.

17. The composition according to claim 14, wherein the organic polymer is a polyolefin and the zinc monoglycerolate at a given loading level in the polyolefin provides a higher crystallisation temperature of the polyolefin than achieved with the same loading level of a zinc monoglycerolate having a crystallite size of greater than 30 nm in the <100> direction or of greater than 60 nm in the <011> direction or having an aspect ratio computed by <100>/<011> coherent domain lengths that is greater than 0.65.

18. The composition according to claim 14, wherein the organic material is an isotactic polypropylene and the zinc monoglycerolate al a given loading level in the isotactic polypropylene pro's/ides a time to achieve 50% polymer crystallisation ($t_{1/2}$) at 140° C. that is at least 40% less than that achieved with the same loading level of a zinc monoglycerolate having a crystallite size greater than at least one of 30 nm in the <100> direction or of greater than 60 nm in the <011> direction, or having an aspect ratio computed by <100>/<011> coherent domain lengths that is greater than 0.65.

19. A process, comprising contacting the zinc monoglycerolate of claim 1 with an organic polymer such that the crystallisation temperature or a least one mechanical property of the organic polymer increases.

20. A nucleating agent, comprising the zinc monoglycerolate of claim 1, which functions as a nucleating agent in an organic polymer.

* * * * *